(12) United States Patent
Mutharasan et al.

(10) Patent No.: US 7,993,854 B2
(45) Date of Patent: Aug. 9, 2011

(54) DETECTION AND QUANTIFICATION OF BIOMARKERS VIA A PIEZOELECTRIC CANTILEVER SENSOR

(75) Inventors: Rajakkannu Mutharasan, West Chester, PA (US); David R. Maraldo, Gilbertsville, PA (US)

(73) Assignee: Drexel University, Philadelphia, PA (US)

( * ) Notice: Subject to any disclaimer, the term of this patent is extended or adjusted under 35 U.S.C. 154(b) by 681 days.

(21) Appl. No.: 12/130,446

(22) Filed: May 30, 2008

(65) Prior Publication Data

US 2009/0078023 A1 Mar. 26, 2009

Related U.S. Application Data

(60) Provisional application No. 60/940,861, filed on May 30, 2007, provisional application No. 60/954,480, filed on Aug. 7, 2007.

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50

(58) Field of Classification Search ........................ None
See application file for complete search history.

(56) References Cited

U.S. PATENT DOCUMENTS

| | | | |
|---|---|---|---|
| 4,186,599 A | 2/1980 | Frick | |
| 4,791,818 A | 12/1988 | Wilde et al. | |
| 5,116,759 A | 5/1992 | Klainer et al. | |
| 5,445,008 A | 8/1995 | Wachter et al. | |
| 5,583,300 A | 12/1996 | Green et al. | |
| 5,719,324 A | 2/1998 | Thundat et al. | |
| 6,170,981 B1 | 1/2001 | Regnier et al. | |
| 6,274,723 B1 | 8/2001 | Nilsen | |
| 6,336,366 B1 | 1/2002 | Thundat et al. | |
| 6,543,274 B1 | 4/2003 | Herrmann et al. | |
| 6,589,727 B1 | 7/2003 | Kleneman et al. | |
| 6,880,402 B1 | 4/2005 | Couet et al. | |
| 7,195,909 B2 | 3/2007 | Kleneman et al. | |
| 7,263,874 B2 | 9/2007 | Fitch et al. | |
| 2003/0194697 A1 | 10/2003 | Kleneman et al. | |
| 2003/0224551 A1 | 12/2003 | Kim et al. | |
| 2005/0063882 A1 | 3/2005 | Centanni et al. | |
| 2005/0112621 A1 | 5/2005 | Kim et al. | |
| 2005/0164299 A1 | 7/2005 | Stewart | |
| 2005/0229677 A1 | 10/2005 | Tuller et al. | |
| 2005/0277852 A1 | 12/2005 | Shih et al. | |
| 2006/0053870 A1 | 3/2006 | Berndt | |
| 2006/0160098 A1 | 7/2006 | Zak et al. | |
| 2006/0196253 A1 | 9/2006 | Crawley et al. | |
| 2006/0223171 A1 | 10/2006 | Craighead et al. | |
| 2006/0228657 A1 | 10/2006 | Masters et al. | |
| 2007/0089515 A1 | 4/2007 | Shih et al. | |
| 2007/0169553 A1 | 7/2007 | Mutharasan et al. | |
| 2007/0218534 A1 | 9/2007 | Kleneman et al. | |
| 2008/0034840 A1 | 2/2008 | Mutharasan et al. | |
| 2008/0035180 A1 | 2/2008 | Mutharasan et al. | |
| 2009/0078023 A1 | 3/2009 | Mutharasan et al. | |

FOREIGN PATENT DOCUMENTS

| | | |
|---|---|---|
| EP | 0631319 A1 | 12/1994 |
| EP | 1536227 A2 | 6/2005 |
| WO | 98/50773 A2 | 11/1998 |
| WO | 2005/043126 A2 | 5/2005 |

OTHER PUBLICATIONS

Campbell, G.A., et al., "Method of Measuring *Bacillus anthracis* spores in the presence of copious amounts of *Bacillus thuringiensis* and *Bacillus cereus*," Anal. Chem., published online Dec. 22, 2006, 79(3), 1145-1152.

Campbell, G.A., et al., "*Escherichia coli* O157:H7 detection limit of millimeter-sized PZT cantilever sensors in 700 cells/mL," Analytical Sci., Apr. 2005, 21, 11-13.

Campbell, G.A., et al., "Detection of pathogen *Escherichia coli* O157:H7 using self-excited PZT-glass microcantilevers," Biosensors and Bioelectronics, Sep. 15, 2005, Epub Dec. 21, 2004, 21(3), 462-473.

Campbell, G.A., et al., "Detect of *Escherichia coli* O157:H7 in ground beef samples using piezoelectric excited millimeter-sized cantilever (PEMC) sensors," Biosens Bioelectron, Feb. 15, 2007, Epub Jul. 10, 2006, 22(7), 1296-1302.

Campbell, G.A., et al.,"A method of measuring *Escherichia coli* O157:H7 at 1 cell/mL in 1 liter sample using antibody functional piezoelectric-excited millimeter-sized cantilever sensor," Environ. Sci. Technol., published online Jan. 23, 2007, 41(5), 1668-1674.

Campbell, G.A., et al., "Detection and quantification of proteins using self-excited PZT-glass millimeter-sized cantilever," Biosensors and Bioelectronics, 2005, 21, 597-607.

Campbell, G.A., et al., "Piezoelectric-excited millimeter-sized cantilever (PEMC) sensors detect *Bacillus anthracis* at 300 spores/mL," Biosensors Bioelectronics, 2006, 21, 1684-1692.

(Continued)

*Primary Examiner* — Lisa Cook
(74) *Attorney, Agent, or Firm* — Woodcock Washburn, LLP

(57) ABSTRACT

Quantification of a target analyte is performed using a single sample to which amounts of the target analyte are added. Calibration is performed as part of quantification on the same sample. The target analyte is detectable and quantifiable using label free reagents and requiring no sample preparation. Target analytes include biomarkers such as cancer biomarkers, pathogenic *Escherichia coli*, single stranded DNA, and staphylococcal enterotoxin. The quantification process includes determining a sensor response of a sensor exposed to the sample and configured to detect the target analyte. Sensor responses are determined after sequential additions of the target analyte to the sample. The amount of target analyte detected by the sensor when first exposed to the sample is determined in accordance with the multiple sensor responses.

6 Claims, 23 Drawing Sheets

OTHER PUBLICATIONS

Campbell, G.A., et al., "Detection of *Bacillus anthracts* spores and a model protein using PEMC sensors in a flow cell at 1 mL/MIN," Biosens Bioelectron, Jul. 15, 2006, Epub Jan. 19, 2006, 22(1), 78-85.

Campbell, G.A., et al., "Detection of airborne *Bacillus anthracis* spores by an integrated system of an air sampler and a cantilever immunosensor," Sensors and Actuators B Chemical, Nov. 15, 2007, available online May 1, 2007, 127(2), 376-382.

Campbell, G.A., et al., "PEMC sensor's mass change sensitivity in 20 PG/HZ under liquid immersion," Biosensors and Bioelectronics, Jul. 15, 2006, Epub Jan. 18, 2006, 22(1), 35-41.

Campbell, G.A., et al., "Use of Piezoelectric-Excited Millimeter-Sized Cantilever Sensors to Measure Albumin Interaction with Self-Assembled Monolayers of Alkanethiols Having Different Functional Headgroups," Anal. Chem., available online Feb. 28, 2006, 78(7), 2328-2334.

Carr, D.W., et al., "Fabrication of nanoelectromechanical systems in single crystal silicon using silicon on insulator substrates and electron beam lithography," J. Vac. Sci. Technology, B, 15(6), 2760-2763.

Maraldo, D., et al., "Method for Quantification of a Prostate Cancer Biomarker in Urine without Sample Preparation," Analytical Chem., Available online Sep. 15, 2007, 79(20), 7683-7690.

Maraldo, D., et al., "Preparation-free method for detecting *Escherichia coli* O157:H7 in the presence of spinach, spring lettuce mix, and ground beef particulates," J. of Food protection, Nov. 2007, 70(11) 2651-2655.

Maraldo, D., et al., "Detection and confirmation of staphylococcal enterotoxin B in apple juice and milk using Piezoelectric-excited Millimeter-sized cantilever (PEMC) sensors at 2.5 femtograms/mL," Analytical Chem., 2007, 79(20) 7636-7643.

Maraldo, D., et al., "10-minute assay for detecting *Escherichia coli* O157:H7 in ground beef samples using piezoelectric-excited millimeter-sized cantilever (PEMC) sensors," J. of Food Protection, 2007, 70(7), 1670-1677.

Maraldo, D. et al., "Method for Label-Free Detection of Femtogram Quantities of Biologics in Flowing Liquid Samples," Anal. Chem., Apr. 1, 2007, 79(7), 2762-2770.

Rijal, K., et al., "PEMC-based method of measuring DNA hybridization at femtomolar concentration directly in human serum and in the presence of copious non-complementary strands," Analytical Chem., 2007, 79, 7392-7400.

Rijal, K., et al., "A method for measuring self-assembly of alkanethiols on gold at femtomolar concentrations," Langmuir, 2007, 23, 6856-6863.

Seung S. Lee, et al., "Self-excited piezoelectric cantilever oscillators," Transducers '95—Eurosensors IX, The $8^{th}$ Int. Conf. on Solid-State Sensors and Actuators, and Eurosensors IX, Stockholm, Sweden, Jun. 25-29, 1995, 417-420.

Wilson, L., et al., "Viscosity and density values from excitation level response of piezoelectric-excited cantilever sensors," Sensors and Actuators A, Jul. 20, 2007, 138, 44-51.

Yi Jeong W. et al., "In situ cell detection using piezoelectric lead zirconate titanate-stainless steel cantilevers," J Applied Physics, Jan. 1, 2003, 93(1), 619-625.

Zhou J. et al., "Zeolite-modified microcantilever gas sensor for indoor air quality control," Sensors and Actuators B, Oct. 1, 2003, 94(3), 337-342.

U.S. Appl. No. 11/747,183 by Mutharasan, et al., filed May 10, 2007.
U.S. Appl. No. 12/130,446 by Mutharasan, et al., filed May 30, 2008.
U.S. Appl. No. 12/141,846 by Mutharasan, et al., filed Jun. 18, 2008.
U.S. Appl. No. 60/746,948 by Mutharasan, filed May 10, 2006.
U.S. Appl. No. 60/746,951 by Mutharasan, et al., filed May 10, 2006.
U.S. Appl. No. 60/807,020 by Mutharasan, et al., filed Jul. 11, 2006.
U.S. Appl. No. 60/944,592 by Mutharasan, filed Jun. 18, 2007.
U.S. Appl. No. 60/954,488 by Mutharasan, filed Aug. 7, 2007.

Maraldo, D, et al., 15-Minute Detection of a Prostate Cancer Biomarker (AMACR) In Voided Urine Samples Using Immuno-Cantilever Sensors, Modern Pathology, vol. 20, No. Suppl. 2, Mar. 2007, p. 352A, XP002525092, and the 96th Annual Meeting of the United States and Canadian Academy of Pathology, San Diego, CA, USA, Mar. 24-30, 2007, ISSN 0893-3952.

PCT International Search Report, PCT/US2008/065295, filed May 30, 2008, mailed Jun. 9, 2009.

DETECTION AND QUANTIFICATION OF BIOMARKERS VIA A PIEZOELECTRIC CANTILEVER SENSOR

CROSS REFERENCE TO RELATED APPLICATIONS

The instant application claims priority to U.S. Provisional Patent Application No. 60/940,861, entitled "PIEZOELECTRIC-EXCITED MILLIMETER-SIZED CANTILEVER," filed May 30, 2007, which is hereby incorporated by reference in its entirety. The instant application also claims priority to U.S. Provisional Patent Application No. 60/954,480, entitled "QUANTIFICATION OF BIOMARKERS IN BODY FLUIDS," filed Aug. 7, 2007, which is hereby incorporated by reference in its entirety.

TECHNICAL FIELD

The technical field generally relates to the detection and quantification of an analyte. More particularly, the technical field relates to the quantification of an analyte in a medium wherein calibration is performed as part of the quantification process.

BACKGROUND

The detection and quantification of biomarkers has various applications, including food and water safety, personalized medicine, and the detection of biothreat agents. In the context of medical diagnostics, detection of biomarkers directly and rapidly in body fluids can significantly decrease health care cost, and possibly improve health care delivery. Current methods have high detection limits and results typically are not available quickly. For example, in medical diagnostics, detection limits are so high that biomarkers are measurable only in an advanced stage of a disease.

Pertaining to personalized medicine, the field of diagnostic proteomics (The analysis of the expression, localizations, functions, and interactions of the proteins expressed by the genetic material of an organism.) has evolved into a powerful method for detecting diseases. The current industry standard in protein diagnostics is enzyme-linked immunosorption assay (ELISA) which has ~pM (picomoles/liter) detection limit and relies on fluorescent labeling. Application of ELISA is limited to a point-of-care setting due to sample preparation and the reliance on maintenance-intensive equipment and skilled personnel. Emerging approaches include immuno-PCR, immunoassay in conjunction with multi-photon detection method (IA-MPD), and super-ELISA. These approaches have disadvantages, such as, requiring sample preparation steps, labeled reagents, multi-step laboratory procedures requiring skilled laboratory personnel, and handling of hazardous materials. For example, super-ELISA requires labeling with multiple copies of a color-generating enzyme and multi-photon detection utilizes radioactive Iodine.

Also pertaining to personalized medicine, prostate cancer is one of the most common forms of cancer among men in the United States and the second leading cause of death. Prostate cancer screening is evolving, with no well-accepted guidelines to date. Currently, prostate cancer is screened using annual serum prostate specific antigen (PSA) evaluation and digital rectal exam (DRE). PSA is the most common biomarker used for the diagnosis and the prediction of staging prostate cancer. PSA screening has led to earlier detection of prostate cancer, however, it is not a cancer-specific marker and, therefore has a low sensitivity and specificity which limit the accurate detection of prostatic adenocarcinoma (malignant tumor). Interpretation of the serum PSA test is made on the basis of PSA levels. Depending on the level of PSA present in serum, the specificity of the PSA test for detecting prostate cancer can be low, because patients with other conditions, such as benign prostatic hyperplasia or chronic prostatitis, also exhibit increased levels of PSA. The use of PSA as an early indicator for prostate cancer has resulted in an increased number of transrectal ultrasound-guided prostate needle biopsies that show small foci of prostatic adenocarcinoma. The diagnosis of small foci of prostatic cancer on needle biopsy is a major diagnostic challenge for surgical pathologists. Both under diagnosis of a small adenocarcinoma and over diagnosis of a benign lesion can cause unnecessary treatment and expense. Additionally, misdiagnosis of a needle biopsy can be a potential liability for pathologists.

SUMMARY

A piezoelectric cantilever sensor is utilized to detect and quantify biomarkers. Quantification is performed using a single sample to which amounts of a biomarker are added. Calibration is performed as part of quantification on the same sample. That is, calibration is performed in situ. No sample preparation is required. An example quantification process includes exposing the piezoelectric cantilever sensor to a medium, wherein the piezoelectric cantilever sensor is configured to bind the biomarker thereto. A resonance frequency of the piezoelectric cantilever sensor is then measured. Next, a first difference between the measured resonance frequency and a baseline frequency is determined. An amount of the biomarker is added to the medium and a second resonance frequency is measured while the medium contains the added amount of the biomarker. A second difference between the second measured resonance frequency and the baseline frequency is determined. A second amount of the biomarker is added to the medium, which still comprises the first amount of biomarker, and a third resonance frequency is measured. Thus, when the third resonance frequency is measured, the medium contains both the first added amount and the second added amount of the biomarker. A third difference between the third measured resonance frequency and the baseline frequency is determined and the amount of biomarker bound to the piezoelectric cantilever sensor prior to addition of the first amount of the biomarker and the second amount of the biomarker is determine in accordance with the first difference, the second difference, and the third difference.

Use of the piezoelectric cantilever sensor provides an easy to use, sensitive, and selective process and system for detection and quantification of biomarkers utilizing a piezoelectric cantilever sensor. The piezoelectric cantilever sensor described herein and utilized to measurement biomarkers provides a higher sensitivity and a shorter time to achieve results than currently available methods including multi-photon immunoassay, super ELISA, and immuno-PCR. Additionally, label-free reagents are used and no sample preparation is required as is often the case with the current methods. The specificity achievable via use of the piezoelectric cantilever sensor is due in part to the vibration of sensor surface and sample flow which reduces non-specific binding.

Utilization of the process and system allows detection and quantification of disease biomarkers directly in body fluids without much sample preparation. The process and system can improve timely diagnostic capability, and allow for earlier identification and treatment of diseases using newly identified biomarkers.

Processes and systems utilizing a piezoelectric cantilever sensor are described herein for detecting and/or quantifying cancer biomarkers, pathogenic *Escherichia coli* (E-coli), DNA hybridization, staphylococcal enterotoxin, or a combination thereof. Sets of experiments utilizing a piezoelectric cantilever sensor and respective results are described. In one set of experiments, the results of rapidly quantifying a prostate cancer biomarker in urine without sample preparation are described. In another set of experiments, the results of detecting a cancer biomarker in serum are described. In another set of experiments, the results of preparation free detection of *Escherichia coli* O157:H7 (EC) in the presence of spinach, spring lettuce mix, and ground beef particulates are described. In another set of experiments, the results of measuring DNA hybridization at femtomolar concentration directly in human serum and in the presence of copious non-complementary strands are described. In another set of experiments, the results of detecting and confirming staphylococcal enterotoxin B in apple juice and milk are described.

BRIEF DESCRIPTION OF THE DRAWINGS

The foregoing summary, as well as the following detailed description, is better understood when read in conjunction with the appended drawings.

DESCRIPTION OF ILLUSTRATIVE EMBODIMENTS

Figure 1:
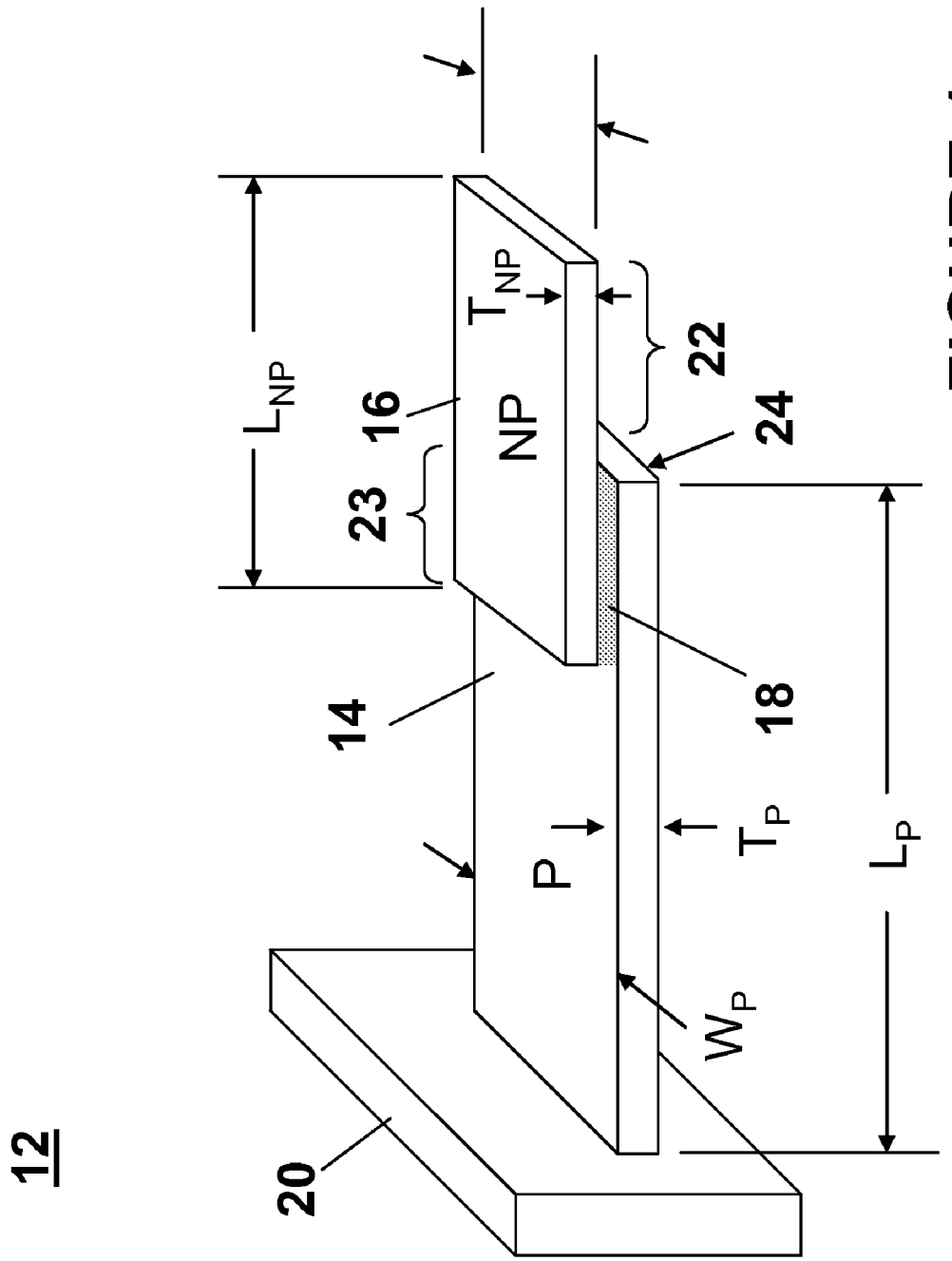
FIG. 1 is an illustration of an example configuration of a self-exciting, self-sensing piezoelectric cantilever sensor.

As described herein, quantification of an amount of a target analyte accumulated on a sensor incorporates calibration of the sensor as part of the quantification process. In an example embodiment, a piezoelectric cantilever sensor is utilized to detect and quantify the target analyte, however, any appropriate sensor can be utilized. Quantification is performed using a single sample to which amounts of the target analyte are added. Calibration is performed as part of quantification on the same sample. The target analyte is detectable using label free reagents and requiring no specific preparation of the sample.

Analytes can comprise any appropriate analyte target material, such as for example, a biomarker, a specific protein, carbohydrate, glycoprotein, protein complex, DNA molecule, cDNA molecule, cRNA molecule, RNA molecule, RNAi molecule, pRNA molecule, mycoplasma, virus, bacterium, yeast, mammalian cell, prions, or phospholipid. As described herein, the ability to detect and quantify incredibly small changes in mass of a target analyte is achieved via the use of a piezoelectric-excited cantilever sensor and binding of recognition molecules as described herein. Example biomarkers include cancer biomarkers, pathogenic *Escherichia coli*, single stranded DNA, and staphylococcal enterotoxin. Recognition molecules can comprise any appropriate recognition molecules such as an antibodies and/or fragments thereof, antigens, receptors or portions thereof, agonists, antagonists, peptides, proteins, carbohydrates, glycoproteins, lipids, phospholipids, or dendrimers which display a high specificity and affinity or avidity to bind a specific analyte, DNA, RNA, or the like. Antibodies can comprise monoclonal antibodies which bind to the target analyte via single binding sites, polyclonal antibodies which bond to the target analyte via multiple binding sites, or any combination thereof. Dendrimers can comprise highly branched molecules that are constructed from interconnecting natural or synthetic monomeric units, e.g., single stranded DNA or RNA, partially denatured double stranded DNA, proteins, such as antibodies, having a DNA or RNA strand attached to it. The highly branched structure can be built through sequential series of hybridization reactions in which monomeric units hybridize to complementary strands. The monomeric units may be labeled with dyes, metals, enzymes, or radioactivity to increase the mass and facilitate detection when bound. The recognition molecules can include unlabeled reagents and/or labeled reagents. A labeled reagent could include any appropriate labeled reagent, such as for example, an antibody with a particle such as metal, latex, or the like.

Utilizing the herein described quantification process, analytes are detectable in body fluids such as urine and serum, and food toxins are detectable in media such as apple juice, spinach, and milk, without preparation of the sample. Also, it has been observed that a cancer biomarker, CA-125, was detectable in quantities as low as 5 femtograms directly without labeling and at 5 attograms with second and third antibody binding.

Sensor Overview

Quantification is described with respect to utilizing a piezoelectric cantilever sensor. To better understand the quantification process and to appreciate the ability to detect and quantify extremely small amounts of mass of a target analyte, a description of an example piezoelectric cantilever sensor is provided.

A self-exciting, self-sensing piezoelectric cantilever sensor can be utilized to detect and measure an analyte immersed in a liquid and an analyte contained in a gas or vacuum. In various example configurations, the piezoelectric cantilever sensor comprises at least one piezoelectric layer and at least one non-piezoelectric layer, wherein the piezoelectric layer is coupled to the non-piezoelectric layer such that the piezoelectric layer and the non-piezoelectric layer are not coextensive. The piezoelectric layer, the non-piezoelectric layer, or both can be coupled to at least one base. The piezoelectric layer and the non-piezoelectric layer can be of varying widths, lengths, and thicknesses.

The piezoelectric cantilever sensor is utilizable to determine the mass of an analyte accumulated thereon. In an example embodiment, a portion of the self-exciting, self-sensing piezoelectric cantilever sensor is placed in a medium (e.g., liquid, gas, vacuum). While in the medium, a resonance frequency of the self-exciting, self-sensing piezoelectric cantilever sensor is measured and compared to a baseline resonance frequency. The difference in the measured resonance frequency and the baseline resonance frequency is indicative of an amount of mass of analyte accumulated (e.g., bound, adsorbed, absorbed) on the self-exciting, self-sensing piezoelectric cantilever sensor.

Analytes can be directly or indirectly bound to the surface of the non-piezoelectric portion, to the piezoelectric portion, or a combination thereof, of the self-exciting, self-sensing piezoelectric cantilever sensor. Binding of an analyte to the non-piezoelectric portion of the self-exciting, self-sensing piezoelectric cantilever sensor results in a change in mass of the self-exciting, self-sensing piezoelectric cantilever sensor, a change in stiffness of the self-exciting, self-sensing piezoelectric cantilever sensor, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the self-exciting, self-sensing piezoelectric cantilever sensor is immersed in a liquid, are detectable and measurable. Resonance frequency changes, wherein at least a portion of the self-exciting, self-sensing piezoelectric cantilever sensor is immersed in a gas or a vacuum, also are detectable and measurable.

The self-exciting, self-sensing piezoelectric cantilever sensor is operable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The self-exciting, self-sensing piezoelectric cantilever sensor is operable at relative high frequencies in liquid media, gas media, and a vacuum. The self-exciting, self-sensing piezoelectric cantilever sensor thus provides extreme sensitivity to mass changes. The self-exciting, self-sensing piezoelectric cantilever sensor is especially suitable for analytes that are present at very low concentrations in media such as in body fluids, water, and food materials, for example.

The self-exciting, self-sensing piezoelectric cantilever sensor described herein provides the ability to detect changes in mass accumulated thereon as small as 100 attogram/Hz (100× $10^{-18}$ grams/Hertz) or less when immersed in a liquid media. Thus, with respect to detecting changes in mass, the self-exciting, self-sensing piezoelectric cantilever sensor is approximately 1 million times more sensitive than a quartz crystal micro-cantilever sensor, approximate 100,000 times more sensitive than standard analytical instruments, and about 100,000 to 1,000,000 times more sensitive than conventional, three-layer piezoelectric cantilever designs.

The self-exciting, self-sensing piezoelectric cantilever sensor permits detection of extremely small concentrations of analyte that bind to the non-piezoelectric portion thereof. Utilizing the self-exciting, self-sensing piezoelectric cantilever sensor, pathogens and proteins are detectable at concentrations as low as a few pathogens/mL and, for proteins of average size (60 kilo-Daltons, kDa), at less than 1 pathogen/mL. Furthermore, any analyte that binds to an organic or inorganic functional group on the non-piezoelectric portion is detectable. The self-exciting, self-sensing piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

Various example applications of the piezoelectric cantilever include the detection of *Bacillus anthracis*, the detection of food-borne pathogens, such as *E. coli* O157:H7, the detection of pathogens in food and water, the detection of certain cell types in body fluids (e.g., circulating tumor cells), the detection of biomarkers in body fluids (e.g., proteins that mark specific pathophysiology such as alpha-fetoprotein, beta-2-microglobulin, bladder tumor antigen, breast cancer marker CA-15-3, and others), the detection of markers of explosives such as trinitrotoluene, the presence of dinitrotoluene, and the detection of airborne and waterborne toxins. The piezoelectric cantilever sensor also can be used for the detection of biological entities at picogram levels, and for the detection of protein-protein interactions, both steady state and kinetic.

Pathogens, such as pathogenic *E. coli* for example, are detectable utilizing the piezoelectric cantilever sensor. Detection of a model protein, lipoprotein, DNA, and/or RNA at a concentration 1.0 femtogram per mL ($10^{-15}$ grams) and pathogens at 1 pathogen/mL, respectively is achievable by measuring directly in liquid using the piezoelectric cantilever sensor immobilized with antibodies specific to the target analyte at a frequency of about 1 to 2 MHz. The self-exciting, self-sensing piezoelectric cantilever sensor is capable of detecting a target analyte without false positives or negatives even when contaminating entities are present. The self-exciting, self-sensing piezoelectric cantilever sensor described herein is particularly advantageous when utilized with a raw sample, and no preparation, concentrating step, and/or enrichment of any type. Detection of an analyte utilizing the piezoelectric cantilever sensor can be conducted directly in raw samples under flow conditions, such as 0.5 to 10.0 mL/minute for example. If clean samples are available, such as in a laboratory environment, detection at 1 femtogram/mL is achievable. This sensitivity is approximately 100 times more sensitive than the sensitivity associated with known optical techniques.

As described herein, the sensitivity of the piezoelectric cantilever sensor is due in part to the geometric design thereof. The relative lengths and widths of the piezoelectric and non-piezoelectric layers of the self-exciting, self-sensing piezoelectric cantilever sensor determine the sensitivity, and also the shape of the peak of the frequency spectrum provided by the self-exciting, self-sensing piezoelectric cantilever sensor. As described in more detail below, the piezoelectric cantilever sensor comprises a piezoelectric layer and a non-piezoelectric layer coupled.

The sensitivity of the piezoelectric cantilever sensor is due in part to utilizing the piezoelectric layer of the cantilever sensor for both actuation and sensing and the electromechanical properties of the piezoelectric layer of the self-exciting, self-sensing piezoelectric cantilever sensor. At resonance, the oscillating cantilever concentrates stress in the piezoelectric layer toward a base portion of the piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

FIG. 1 is an illustration of a self-exciting, self-sensing piezoelectric cantilever sensor 12 comprising a piezoelectric portion 14 and a non-piezoelectric portion 16. Piezoelectric portions are labeled with an uppercase letter p ("P"), and non-piezoelectric portions are labeled with the uppercase letters np ("NP"). The self-exciting, self-sensing piezoelectric cantilever sensor 12 depicts an embodiment of an unanchored, overhang, self-exciting, self-sensing piezoelectric cantilever sensor. The self-exciting, self-sensing piezoelectric cantilever sensor 12 is termed "unanchored" because the non-piezoelectric layer 16 is not attached to the base portion 20. The self-exciting, self-sensing piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoelectric ceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 10 micrometers ($10 \times 10^{-6}$ meters) to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
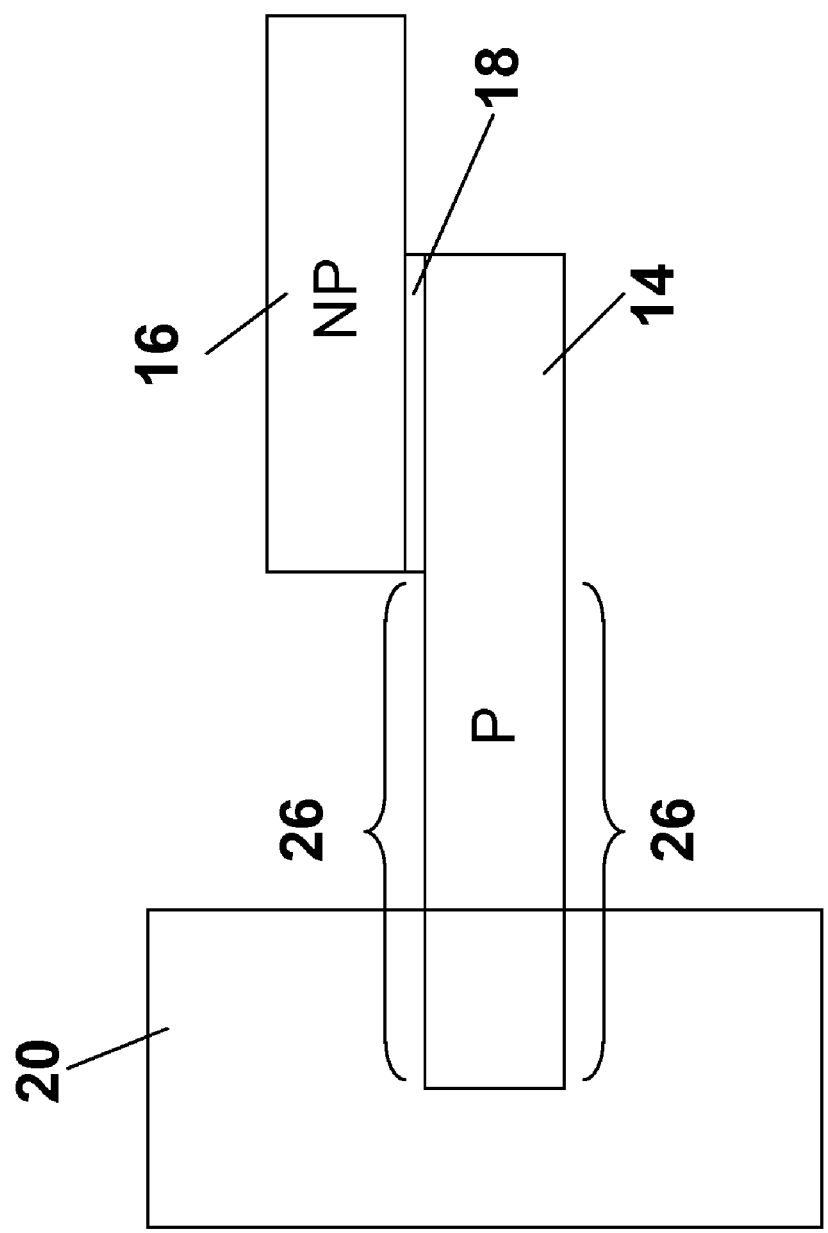
FIG. 2 is a cross-sectional view of an example self-exciting, self-sensing piezoelectric cantilever sensor depicting electrode placement regions for electrodes operationally associated with the piezoelectric layer.
Figure 3:
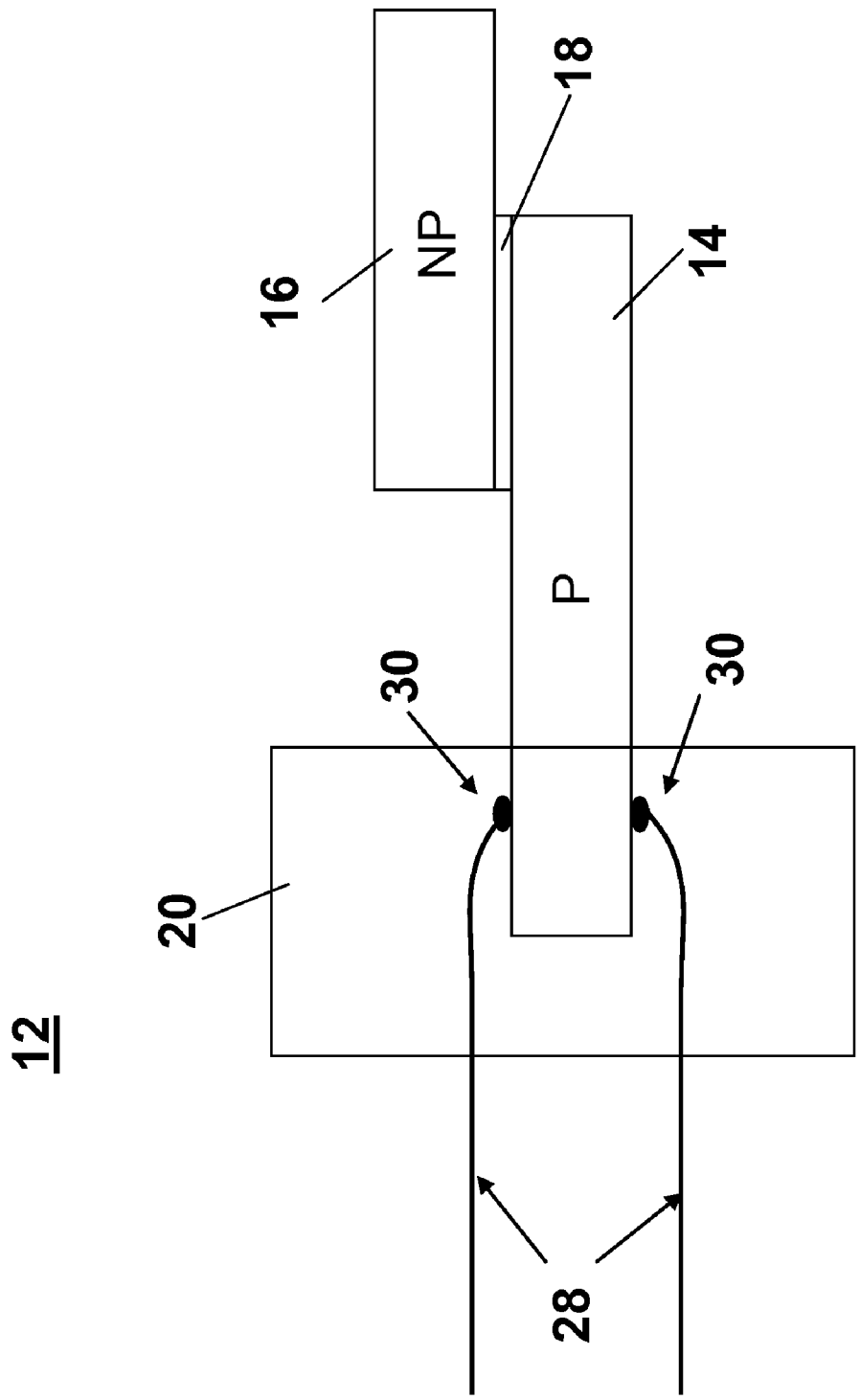
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
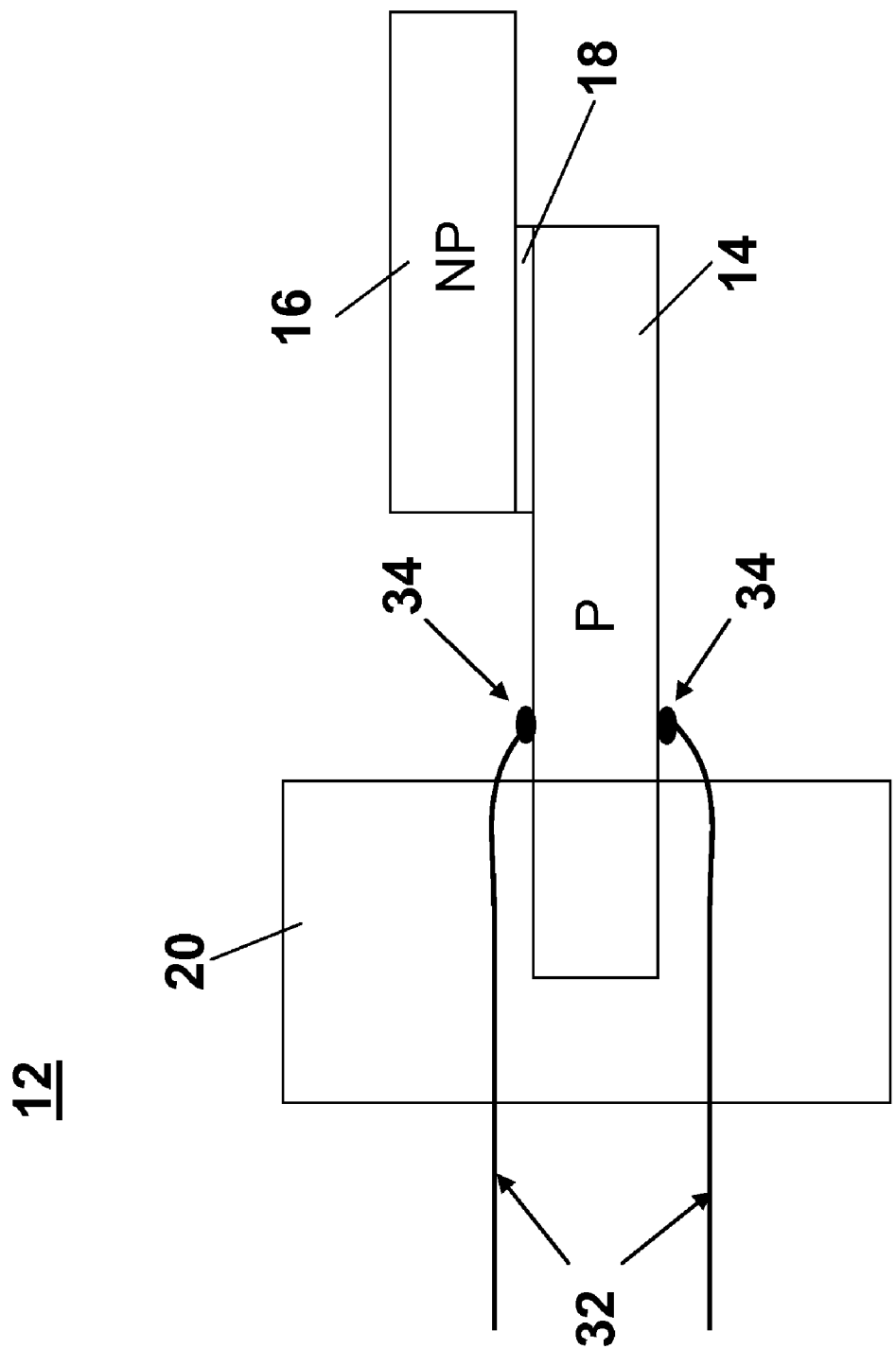
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the self-exciting, self-sensing piezoelectric cantilever sensor 12 depicting electrode placement regions 26 for electrodes operationally associated with the piezoelectric portion 14. Electrodes can be placed at any appropriate location on the piezoelectric portion of the self-exciting, self-sensing piezoelectric cantilever sensor as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the self-exciting, self-sensing piezoelectric cantilever sensor is due in part to advantageously directing (concentrating) the stress in the piezoelectric layer 14 and placing electrodes proximate thereto. The configurations of the self-exciting, self-sensing piezoelectric cantilever sensor described herein (and variants thereof) tend to concentrate oscillation associated stress in the piezoelectric layer 14. At resonance, in some of the configurations of the self-exciting, self-sensing piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more bendable) allows for exploitation of the associated shift in resonance frequency to detect extremely small changes in mass of the self-exciting, self-sensing piezoelectric cantilever sensor. Thus, in example configurations of the self-exciting, self-sensing piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the self-exciting, self-sensing piezoelectric cantilever sensor. In other example configurations of the self-exciting, self-sensing piezoelectric cantilever sensor electrodes are positioned proximate the location of concentrated stress in the piezoelectric layer regardless of the proximity of the concentrated stress to a base portion of the self-exciting, self-sensing piezoelectric cantilever sensor.

Figure 5:
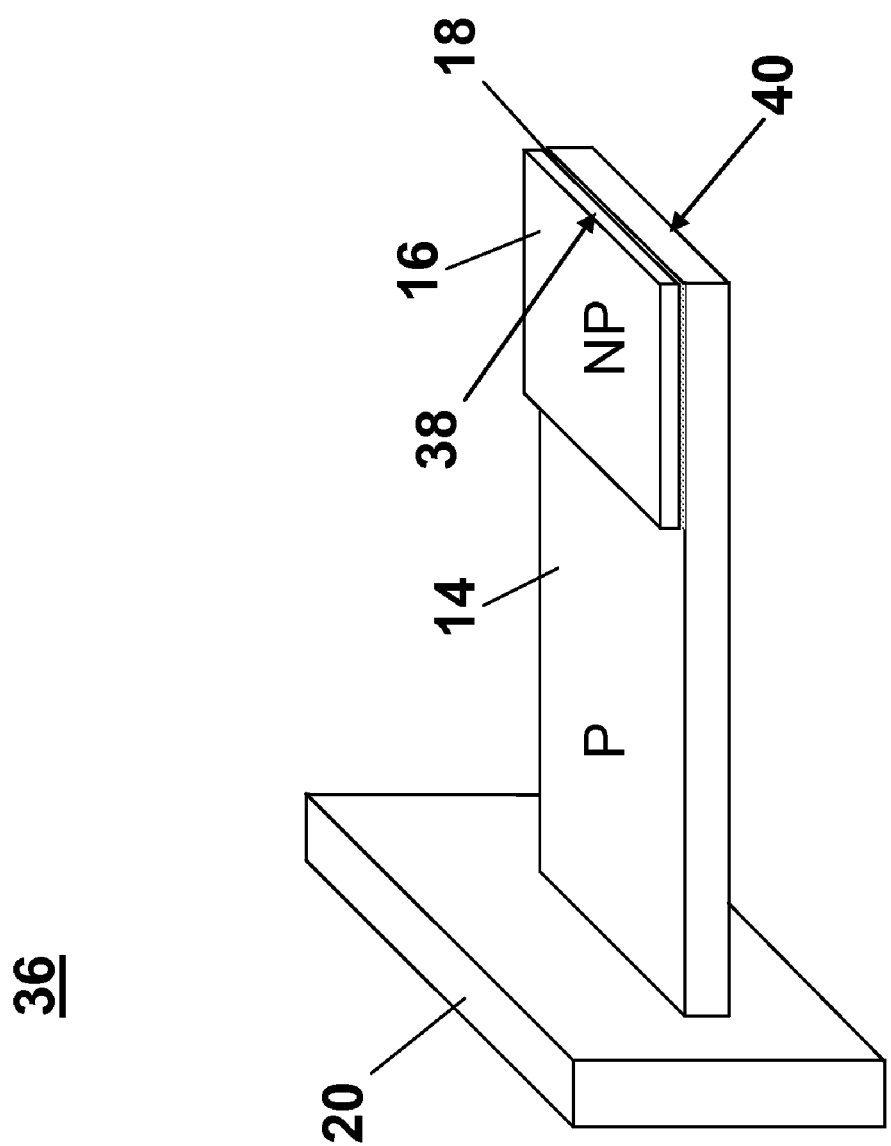
FIG. 5 is an illustration of an example configuration of a self-exciting, self-sensing piezoelectric cantilever sensor wherein the distal end of the piezoelectric layer is flush with the distal end of the non-piezoelectric layer.

The self-exciting, self-sensing piezoelectric cantilever sensor can be configured in accordance with a plurality of configurations, some of which are depicted in FIG. 5 through FIG. 16. It is to be understood however, that the configurations depicted herein do not represent all possible configurations, but rather a representative sample of configurations of the self-exciting, self-sensing piezoelectric cantilever sensor. FIG. 5 is an illustration of an example configuration 36 of an unanchored self-exciting, self-sensing piezoelectric cantilever sensor wherein the distal end 40 of the piezoelectric portion 14 is flush with the distal end 38 of the non-piezoelectric portion 16. The self-exciting, self-sensing piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

Figure 6:
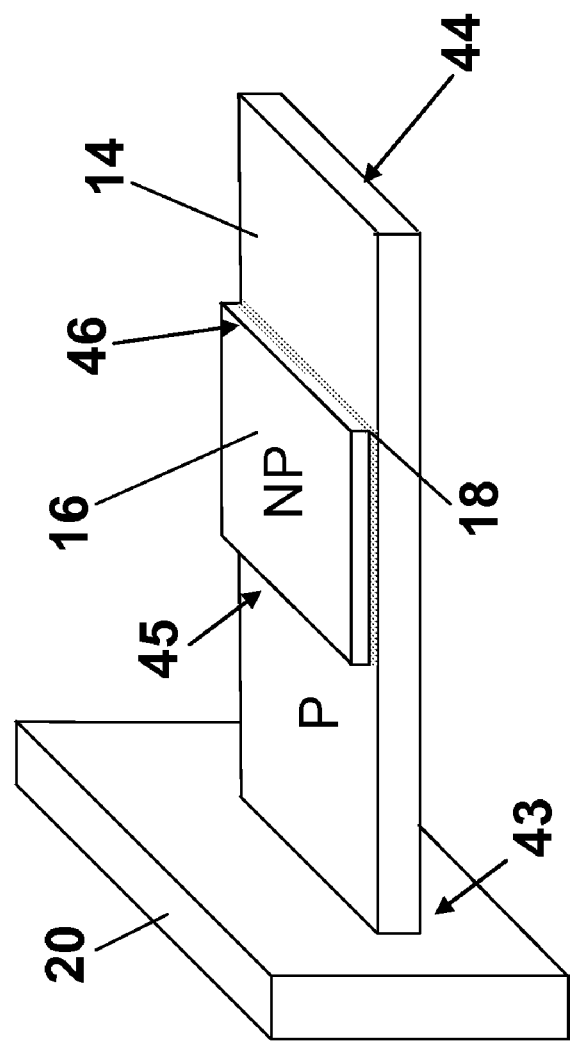
FIG. 6 is an illustration of an example configuration of a self-exciting, self-sensing piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

FIG. 6 is an illustration of an example configuration 42 of an unanchored self-exciting, self-sensing piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

The self-exciting, self-sensing piezoelectric cantilever sensor also can be configured to comprise multiple base portions. Example configurations of the self-exciting, self-sensing piezoelectric cantilever sensor comprising multiple base portions are depicted in FIG. 7 through FIG. 14. Configuring the self-exciting, self-sensing piezoelectric cantilever sensor to comprise multiple base portions is not intuitive because the expectation of one skilled in the art would be that affixation of both ends of the self-exciting, self-sensing piezoelectric cantilever sensor would provide a poor response as a result of the restrictions of the displacement of the self-exciting, self-sensing piezoelectric cantilever sensor as a result of its affixation to the multiple base portions. For configurations of the self-exciting, self-sensing piezoelectric cantilever sensor comprising two base portions, in an example embodiment, the stress of in the piezoelectric portion is measured, rather than the displacement of the piezoelectric portion. Configuring the self-exciting, self-sensing piezoelectric cantilever sensor to comprise two base portions provides a stable and robust sensor that can perform under relatively high media flow conditions and provide excellent mass change sensitivity. Along with providing a mechanically robust self-exciting, self-sensing piezoelectric cantilever sensor that can withstand a relatively wide range of media flow conditions with minimal determination in performance, configuring the self-exciting, self-sensing piezoelectric cantilever sensor to comprise two base portions provides a fundamental frequency (e.g., greater than 100 kHz) that is three to four times higher than a cantilever sensor having a single base portion and of similar dimensions.

Figure 7:
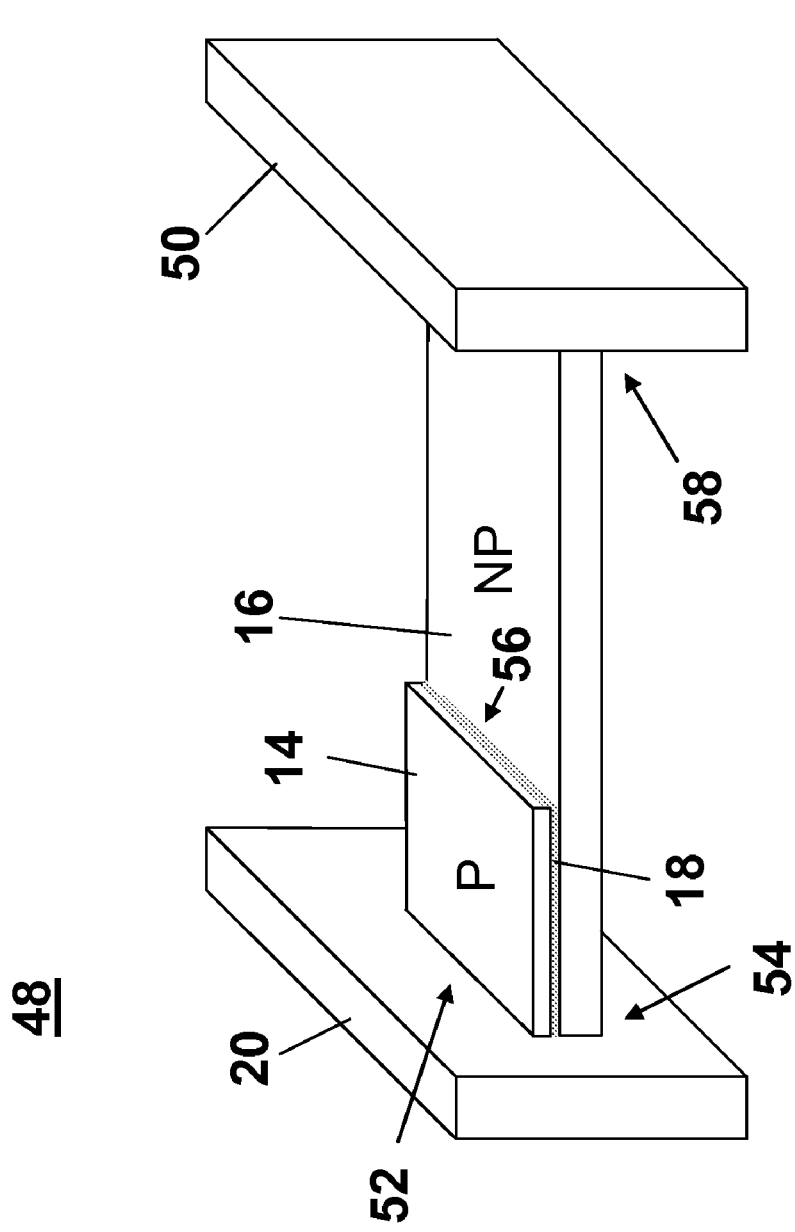
FIG. 7 is an illustration of an example configuration of a self-exciting, self-sensing piezoelectric cantilever sensor having two base portions.

FIG. 7 is an illustration of an example configuration 48 of an anchored self-exciting, self-sensing piezoelectric cantilever sensor comprising two base portions 20, 50. The self-exciting, self-sensing piezoelectric cantilever sensor 48 is termed "anchored" because the non-piezoelectric portion 16 is attached to the base portion 20. In the configuration depicted in the self-exciting, self-sensing piezoelectric cantilever sensor 48, both the proximate end 52 of the piezoelectric portion 14 and the proximate end 54 of the non-piezoelectric portion 16 are attached to the base portion 20. The piezoelectric portion and the non-piezoelectric portion can be attached to the base portion via any appropriate means. The distal end 58 of the non-piezoelectric portion 16 also is attached to the base portion 50. The distal end 58 of the non-piezoelectric portion 16 extends beyond the distal portion 56 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 8:
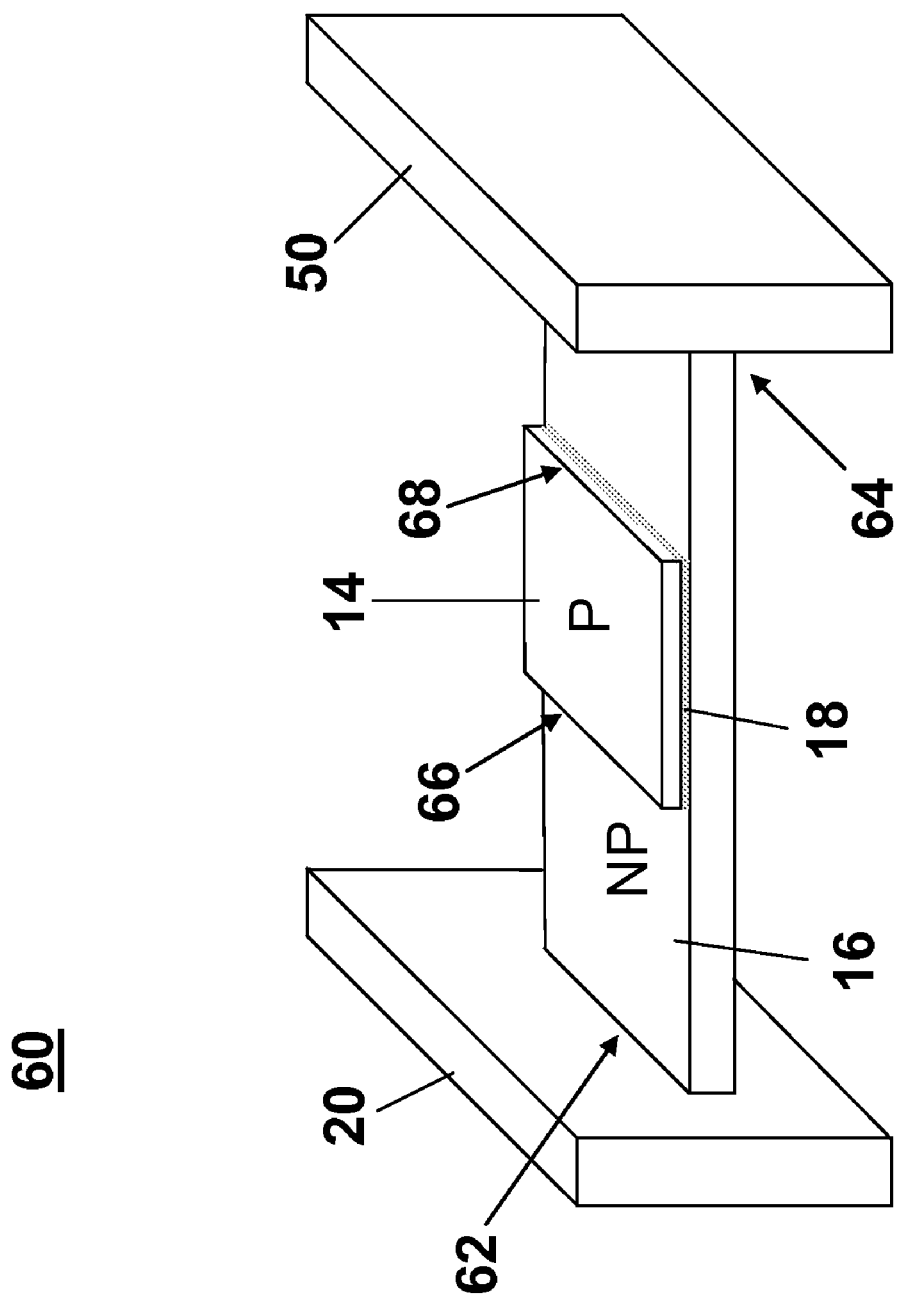
FIG. 8 is an illustration of another example configuration of a self-exciting, self-sensing piezoelectric cantilever sensor, wherein the piezoelectric layer is not attached to either base portion.

FIG. 8 is an illustration of an example configuration 60 of an anchored self-exciting, self-sensing piezoelectric cantilever sensor comprising two base portions 20, 50, wherein the piezoelectric portion 14 is not attached to either base portion 20 or base portion 50. In the configuration depicted in the self-exciting, self-sensing piezoelectric cantilever sensor 60, the proximate end 62 of the non-piezoelectric portion 16 is attached to the base portion 20 and the distal end 64 of the non-piezoelectric portion 16 is attached to the base portion 50. The proximate end 62 of the non-piezoelectric portion 16 extends beyond the proximate end 66 of the piezoelectric portion 14 and the distal end 64 of the non-piezoelectric portion 16 extends beyond the distal end 68 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 9:
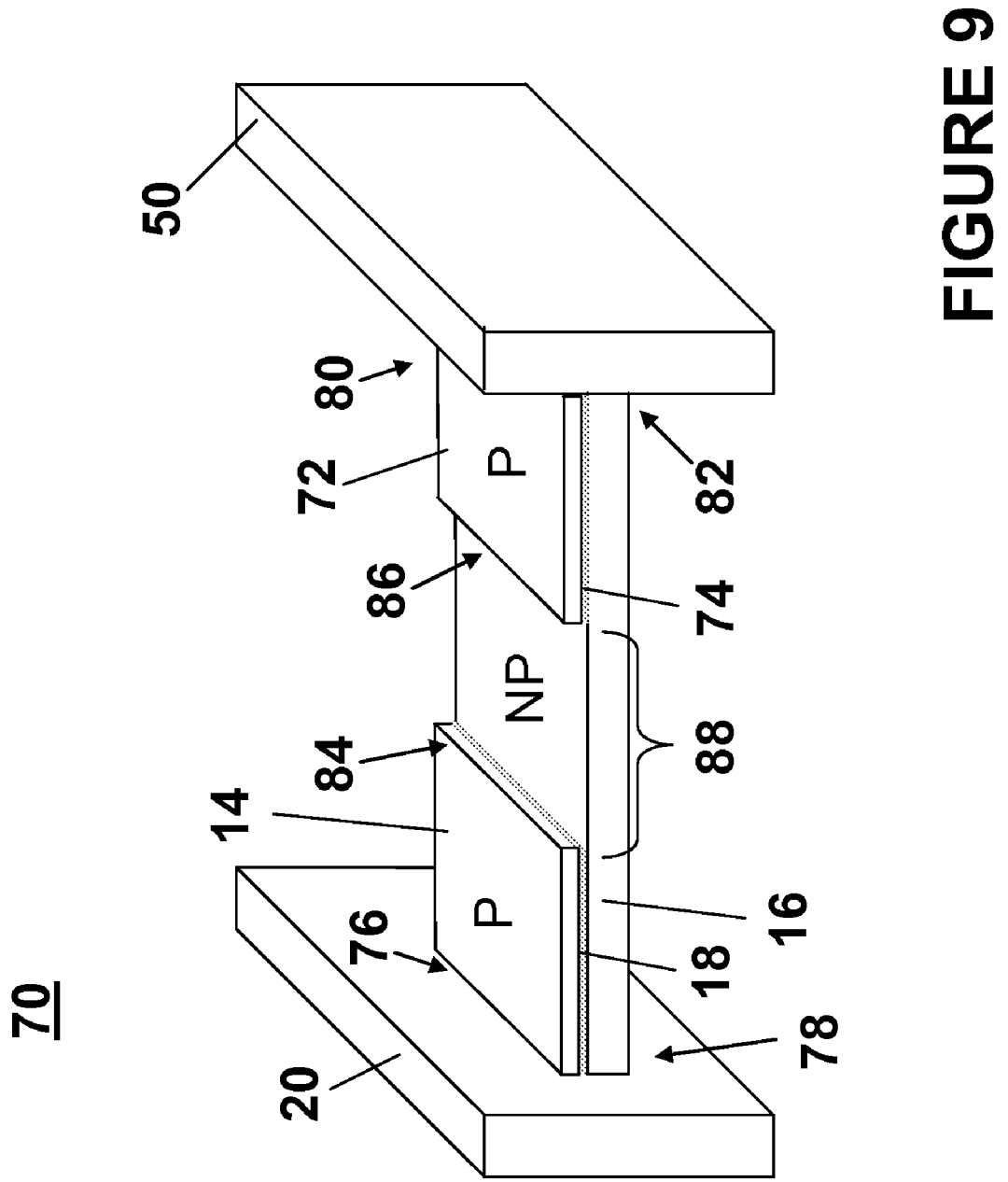
FIG. 9 is an illustration of an example configuration of a self-exciting, self-sensing piezoelectric cantilever sensor having the piezoelectric layer anchored at two ends.

FIG. 9 is an illustration of an example configuration 70 of an anchored self-exciting, self-sensing piezoelectric cantilever sensor comprising two base portions 20, 50, comprising two piezoelectric portions 14, 72, and comprising two adhesive portions 18, 74. In the configuration depicted in the self-exciting, self-sensing piezoelectric cantilever sensor 70, the proximate end 76 of the piezoelectric portion 14 and the proximate end 78 of the non-piezoelectric portion 16 are attached to the base portion 20. The distal end 80 of the piezoelectric portion 72 and the distal end 82 of the non-piezoelectric portion 16 are attached to the base portion 50. The proximate end 78 of the non-piezoelectric portion 16 extends beyond the proximate end 86 of the piezoelectric portion 72. The distal end 82 of the non-piezoelectric portion 16 extends beyond the distal end 84 of the piezoelectric portion 14. The distal end 84 of the piezoelectric portion 14 and the proximate end 86 of the piezoelectric portion 72 form a space 88 therebetween. The piezoelectric portion 14 is coupled to the non-piezoelectric portion 16 via adhesive portion 18. The piezoelectric portion 72 is coupled to the non-piezoelectric portion 16 via adhesive portion 74. The adhesive portions 18 and 74 are positioned, respectively, between the overlapping portions of the piezoelectric portion 14 and the non-piezoelectric portion 16, and the piezoelectric portion 72 and the non-piezoelectric portion 16.

Figure 10:
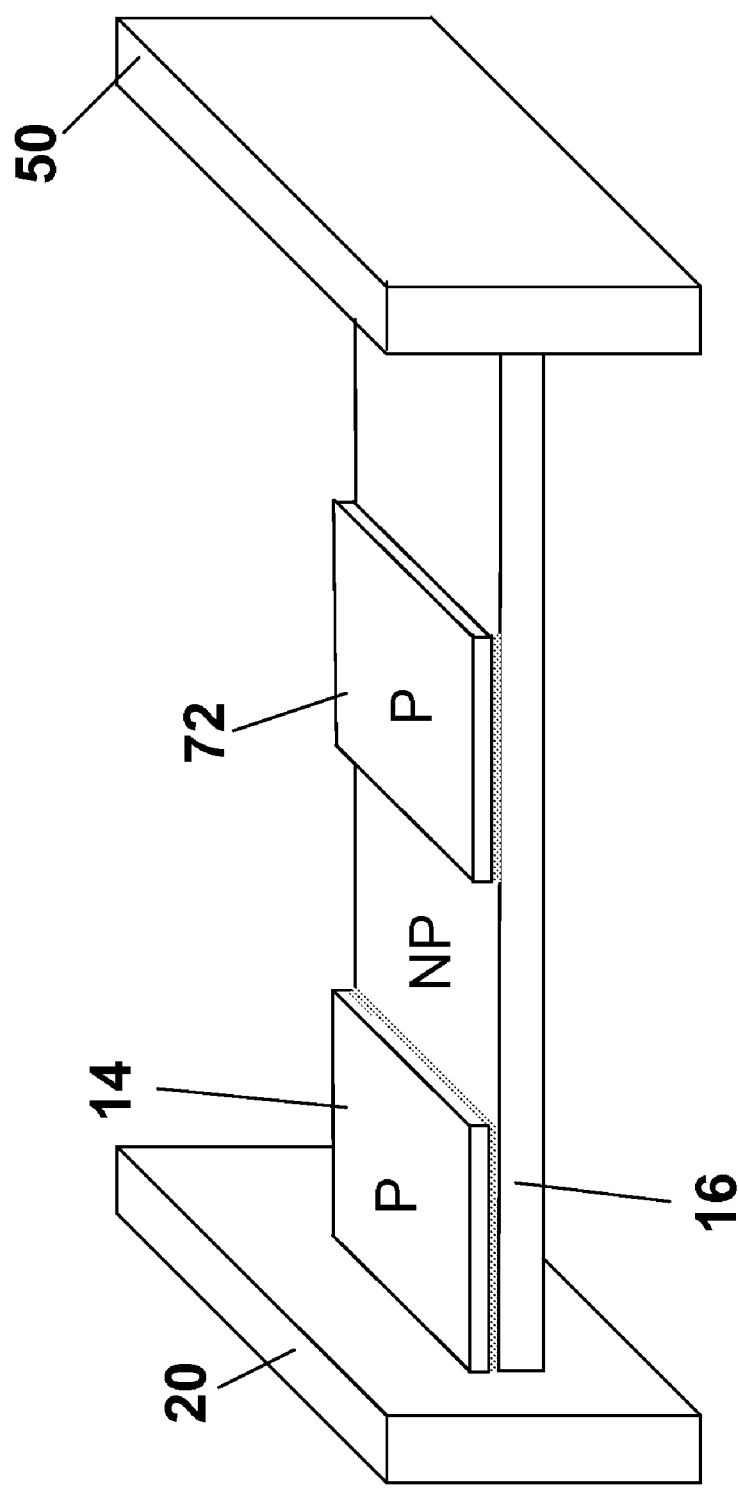
FIG. 10 is an illustration of an example configuration of a self-exciting, self-sensing piezoelectric cantilever sensor wherein the piezoelectric layer comprises two portions, one of which is anchored.
Figure 11:
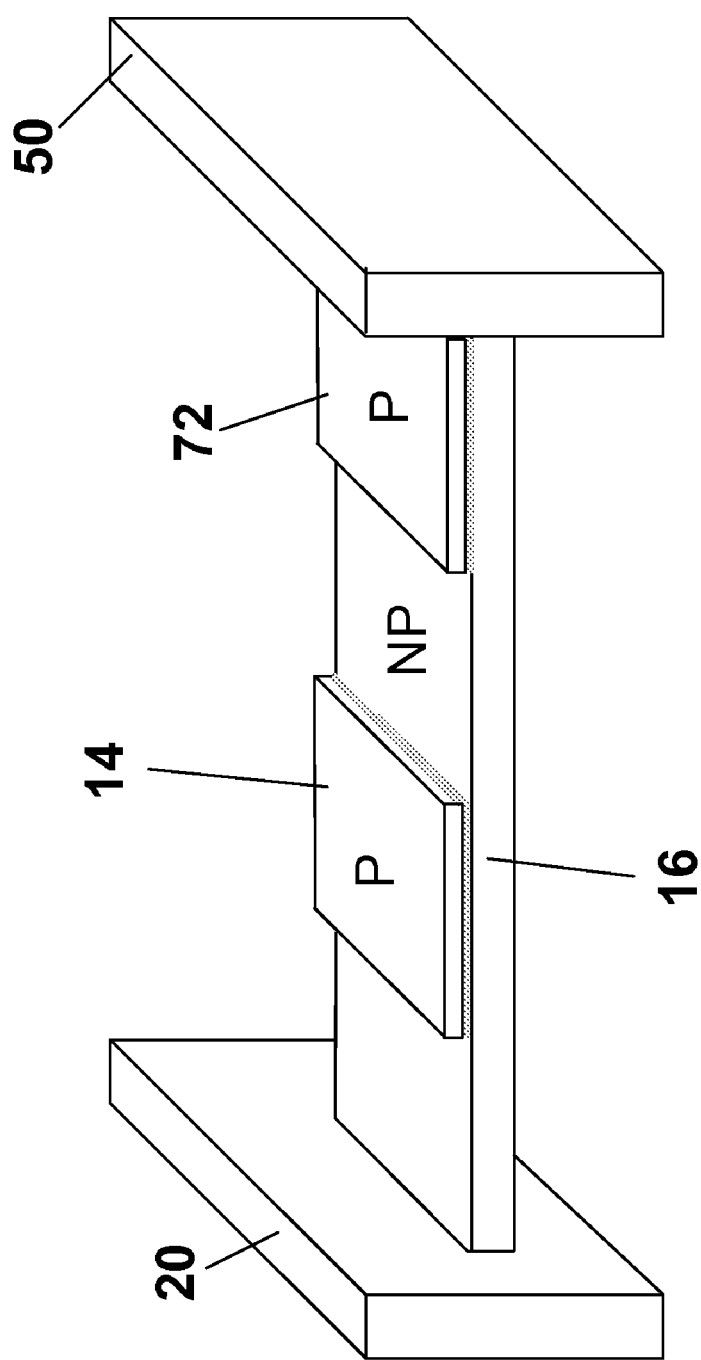
FIG. 11 is another illustration of an example configuration of a self-exciting, self-sensing piezoelectric cantilever sensor wherein the piezoelectric layer comprises two portions, one of which is anchored.
Figure 12:
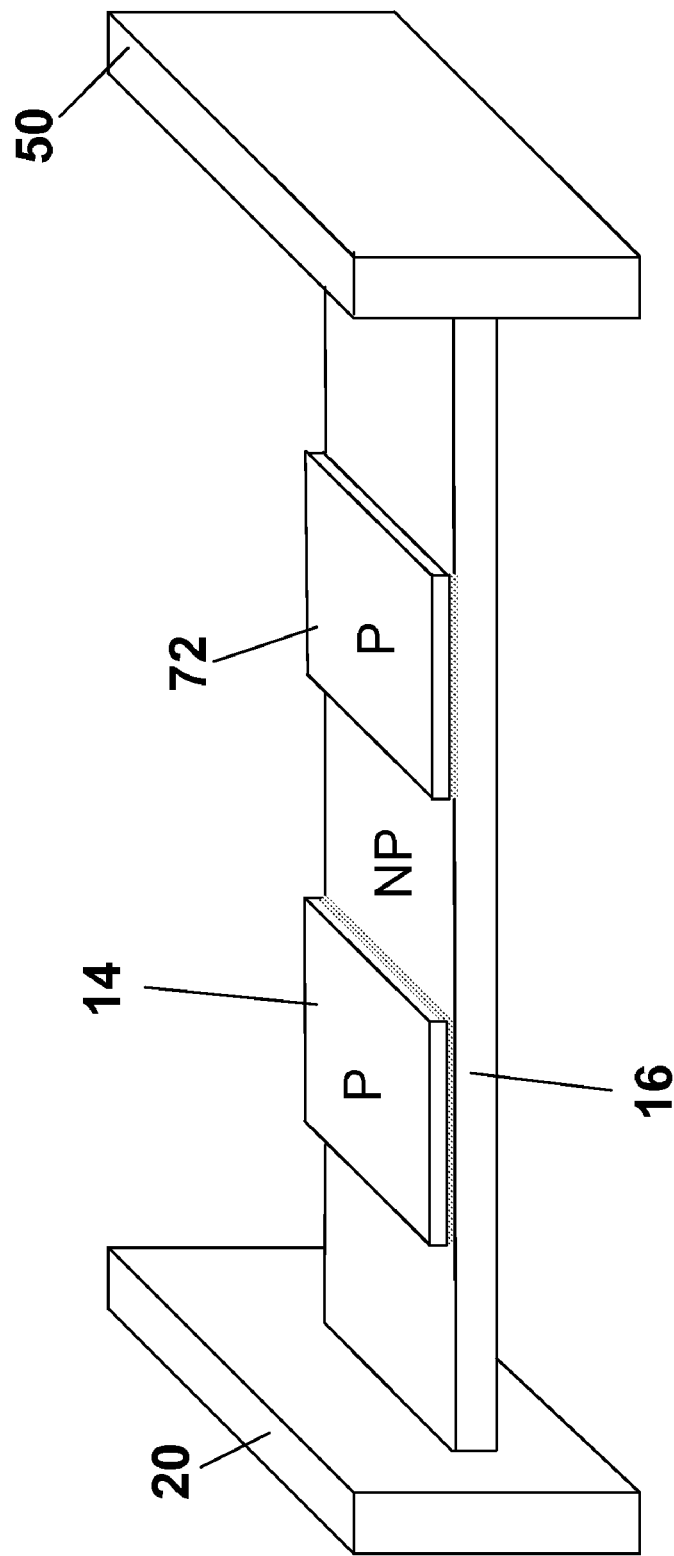
FIG. 12 is an illustration of an example configuration of a self-exciting, self-sensing piezoelectric cantilever sensor wherein the piezoelectric layer comprises two portions, neither which is anchored.

In various alternate example configurations of the configuration 70 depicted in FIG. 9, only one of the piezoelectric portions 14, 72 is attached to a respective base portion 20, 50. For example, in one example configuration as depicted in FIG. 10, the piezoelectric portion 14 is attached to the base portion 20 and the piezoelectric portion 72 is not attached to the base portion 50. In another example configuration, as depicted in FIG. 11, the piezoelectric portion 72 is attached to the base portion 50 and the piezoelectric portion 14 is not attached to the base portion 20. In yet another example configuration, as depicted in FIG. 12, neither the piezoelectric portion 14 nor the piezoelectric portion 72 is attached to a respective base portion 20, 50. In the various example configurations in which a piezoelectric layer comprises multiple portions, electrodes can be attached to any appropriate piezoelectric portion or portions. For example, in the example configuration depicted in FIG. 9, FIG. 10, FIG. 11, and FIG. 12, electrodes can be attached to piezoelectric portion 14, piezoelectric portion 72, or a combination thereof.

Figure 13:
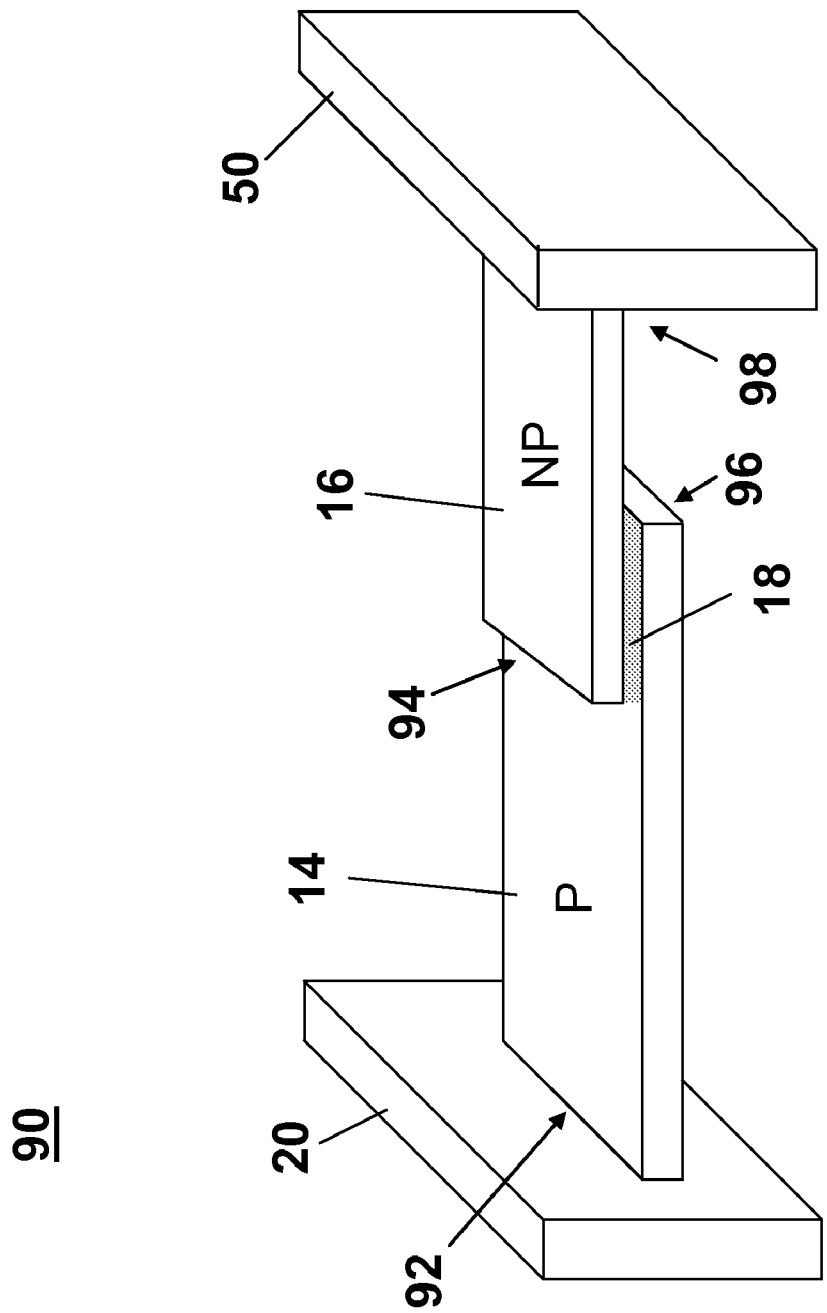
FIG. 13 is an illustration of an example configuration of a self-exciting, self-sensing piezoelectric cantilever sensor having an anchored non-piezoelectric portion and a non-anchored piezoelectric portion.

FIG. 13 is an illustration of an example configuration 90 of an anchored self-exciting, self-sensing piezoelectric cantilever sensor comprising two base portions 20, 50, wherein the piezoelectric portion 14 is attached to the base portion 20 and the non-piezoelectric portion 16 is attached to the base portion 50. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The distal end 98 of the non-piezoelectric portion 16 extends beyond the distal end 96 of the piezoelectric portion 14. The proximate end 92 of the piezoelectric portion 14 extends beyond the proximate end 94 of the non-piezoelectric portion 16.

Figure 14:
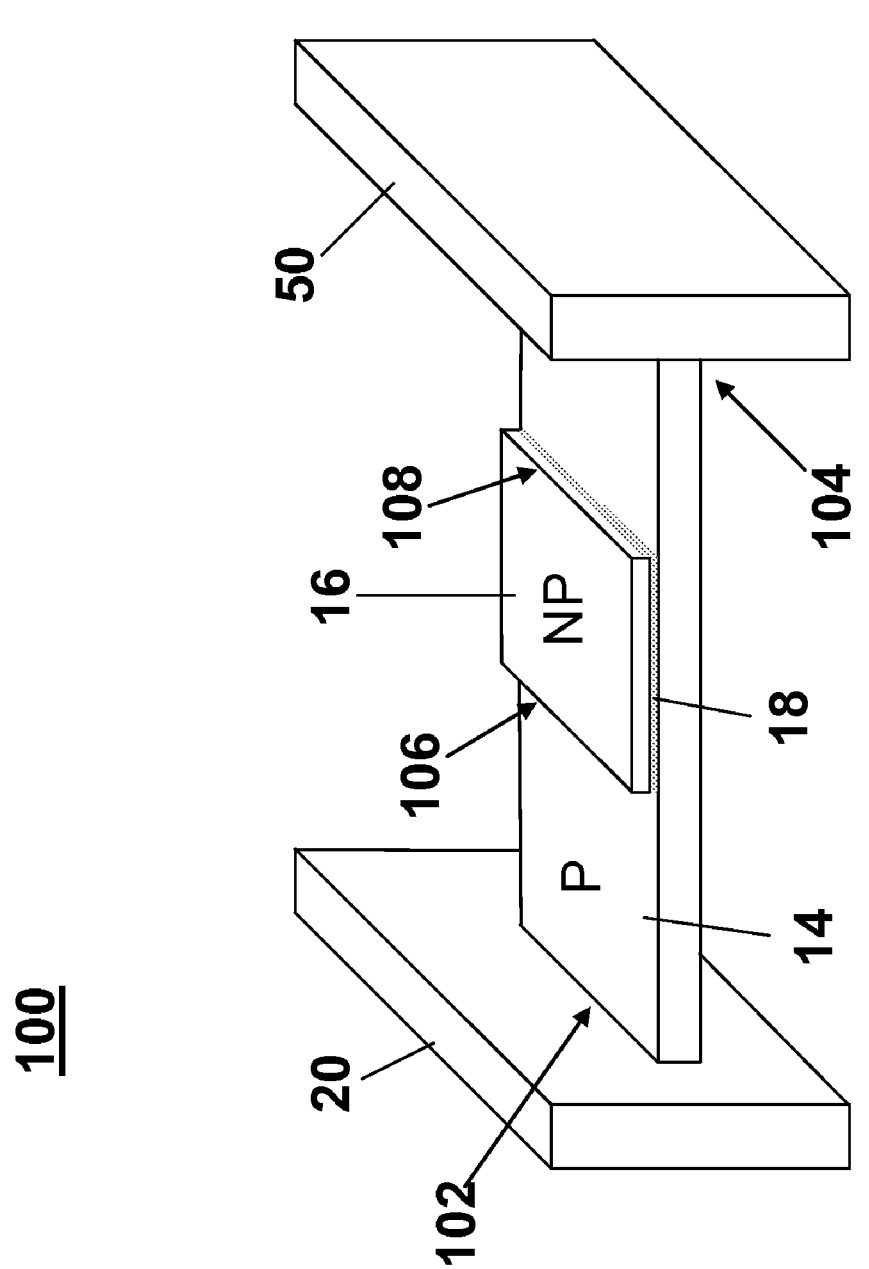
FIG. 14 is an illustration of an example configuration of a self-exciting, self-sensing piezoelectric cantilever sensor, wherein the non-piezoelectric layer is not attached to either base portion.

FIG. 14 is an illustration of an example configuration 100 of an anchored self-exciting, self-sensing piezoelectric cantilever sensor comprising two base portions 20, 50, wherein the non-piezoelectric portion 16 is not attached to either base portion 20 or base portion 50. In the configuration depicted in the self-exciting, self-sensing piezoelectric cantilever sensor 100, the proximate end 102 of the piezoelectric portion 14 is attached to the base portion 20 and the distal end 104 of the piezoelectric portion 14 is attached to the base portion 50. The proximate end 102 of the piezoelectric portion 14 extends beyond the proximate end 106 of the non-piezoelectric portion 16 and the distal end 104 of the piezoelectric portion 14 extends beyond the distal end 108 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 15:
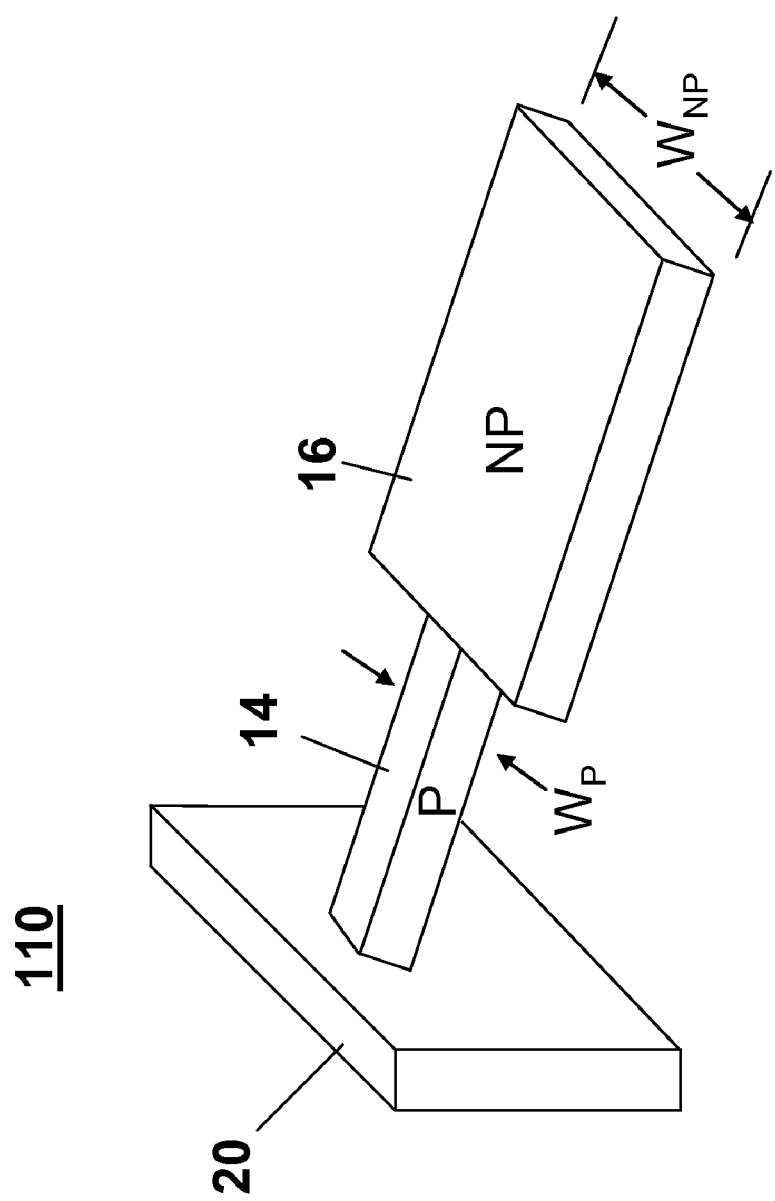
FIG. 15 is illustration of another example configuration of a self-exciting, self-sensing piezoelectric cantilever sensor wherein the piezoelectric portion has a different width than the piezoelectric portion.

FIG. 15 is an illustration of an example configuration 110 of an unanchored self-exciting, self-sensing piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16. The configuration 110 depicted in FIG. 15 is similar to the configuration 12 depicted in FIG. 1, with the exception that $W_P$ is less than $W_{NP}$. According, the self-exciting, self-sensing piezoelectric cantilever sensor 110 depicts an embodiment of an unanchored, overhang, self-exciting, self-sensing piezoelectric cantilever sensor. The piezoelectric portion 14 is coupled to the non-piezoelectric portion 16 via adhesive portion (adhesive portion not shown in FIG. 15). The adhesive portion is positioned between the overlapping portions of the piezoelectric portion 14 and the non-piezoelectric portion 16. The piezoelectric portion 14 is coupled to a base portion 20.

Figure 16:
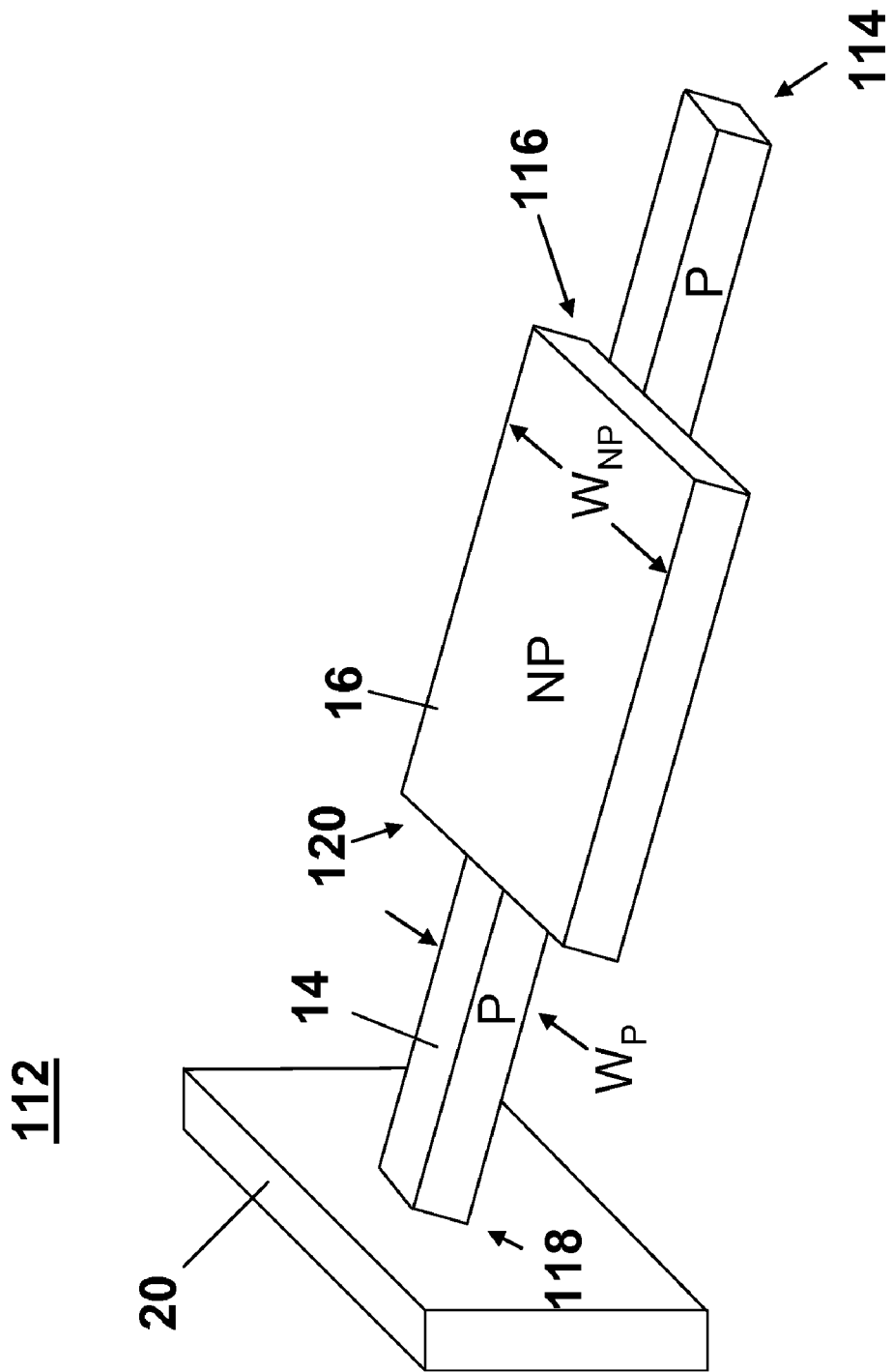
FIG. 16 is an illustration of an example configuration of a self-exciting, self-sensing piezoelectric cantilever sensor comprising a piezoelectric layer and a non-piezoelectric layer, wherein the width, of the piezoelectric layer is less than the width of the non-piezoelectric layer 16, and the distal end of the piezoelectric layer extends beyond the distal end of the non-piezoelectric layer and the proximate end of the piezoelectric layer extends beyond the proximate end of the non-piezoelectric layer.

FIG. 16 is an illustration of an example configuration 112 of an unanchored self-exciting, self-sensing piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16, and wherein the distal end 114 of the piezoelectric portion 14 extends beyond the distal end 116 of the non-piezoelectric portion 16 and the proximate end 118 of the piezoelectric portion 14 extends beyond the proximate end 120 of the non-piezoelectric portion 16. The configuration 112 depicted in FIG. 16 is similar to the configuration 42 depicted in FIG. 6, with the exception that $W_P$ is less than $W_{NP}$. The piezoelectric portion 14 is coupled to the non-piezoelectric portion 16 via adhesive portion (adhesive portion not shown in FIG. 16). The adhesive portion is positioned between the overlapping portions of the piezoelectric portion 14 and the non-piezoelectric portion 16. The piezoelectric portion 14 is coupled to the base portion 20.

The piezoelectric cantilever sensor is not to be confused with resonating or bending mode microcantilevers. The piezoelectric cantilever sensor is not a microcantilever and is not an AFM (atomic force microscope) inspired device. The piezoelectric cantilever sensor does not operate in the bending mode. The piezoelectric cantilever sensor is self-sensing and is self-actuating, which is advantageous from a measurement and cost perspective.

In operation, the direct piezoelectric effect is utilized to excite the cantilever, and the same PZT film senses the resulting response. In an example configuration the PZT film is bonded to a base glass cantilever forming a composite cantilever. When an electric field is applied across the thickness of the PZT film, it extends along its length causing the underlying glass to bend. If the applied field is alternated periodically, the composite cantilever vibrates. The natural frequency of the cantilever depends on the flexural modulus and mass density of the composite cantilever. At resonance, the cantilever undergoes higher stresses when the exciting electric field is at the mechanical resonance frequency. The PZT layer exhibits a sharp change in electrical impedance and can be followed by the phase angle measurement. The sensitivity of the piezoelectric cantilever sensor has been measured to be in the range of 0.3 to 2 fg/Hz. The implication of this finding is that attachment of a few million 60 kDa molecules can be measured. For example, experimentation shows that 5 attograms of the ovarian cancer biomarker, CA-125 is successfully detected in spiked-serum samples. Five attograms is ~100 molecules.

Figure 17:
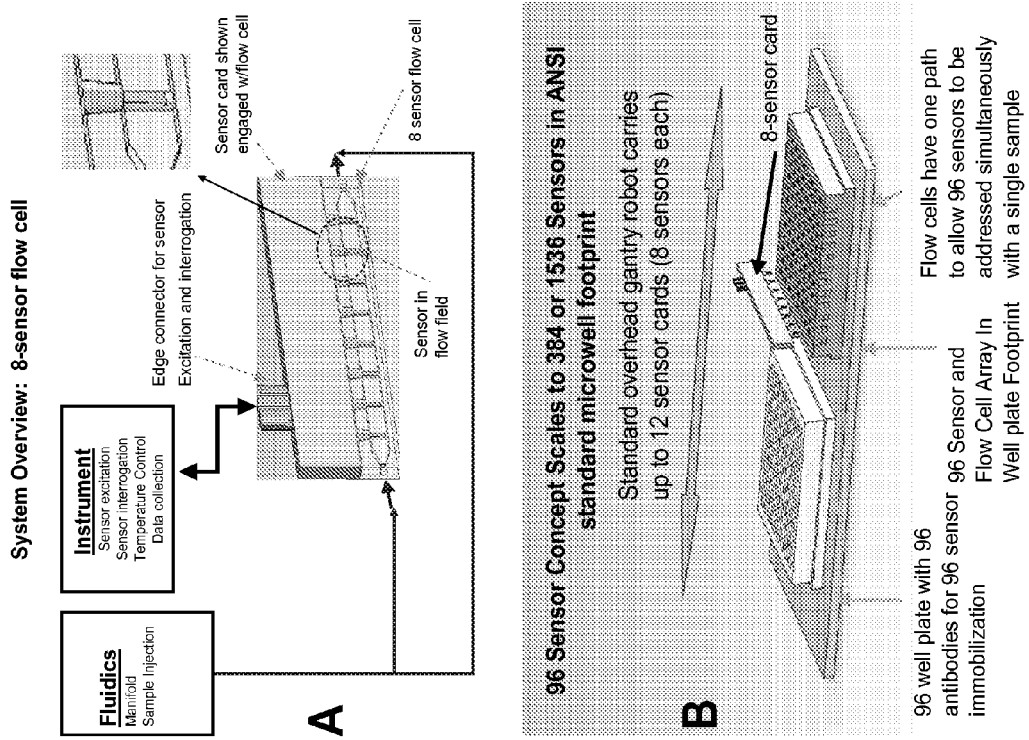
FIG. 17 is a schematic depiction of an example a scalable 8-sensor array module system.

FIG. 17 is a schematic depiction of an example a scalable 8-sensor array module system. The 8-PEMC sensor array module system depicted in FIG. 17 possesses the following criterion: (1) Scalability. As shown in FIG. 17, the sensor-array can be scaled to 384 or 1536 sensors in a standard micro-well footprint. (2) Multiplexing. The sensor-array allows a single sample to pass through all sensors in a single flow path. Each sensor can be immobilized with a different antibody specific to a particular target. (3) Automation. In the case of a 96, 384 or 1536 format, each sensor can be immobilized with a unique antibody and then integrated into a single flow cell path in a fully automated fashion. The system can use standard liquid handling robots and platforms. (4) Minimum hold-up volume. The hold-up volume in the flow system will be minimized. (5) Temperature Control. The sample fluid will be kept at a constant temperature.

The basic building blocks of the system depicted in FIG. 17 comprise an 8-PEMC sensor array module and a mating flow cell. In an example embodiment, the sensor module will have 8 sensors spaced according to the ANSI and the Society of Biomolecular Screening (SBS) standards. Each sensor mates with the flow cell via a luer taper fitting. The sensor frame has an electrical edge connector to carry signals to and from the sensors. In a full 96, 384, or 1536 format system a series of sensor cards will be plugged into an overhead trolley. The trolley will carry the sensor heads to a standard-sized microwell for antibody immobilization and rinse procedures. The trolley will then travel to the sensor flow cell array and be engaged with the flow cell. Once engaged, the sample (~a few mL) will be injected into the flow cell so that a single sample can be interrogated by all sensors in the system in a once through flow format or in a recirculation mode. The flow cells are designed to minimize hold-up volume; the volume between sensors can be as little as 300 nl in the 1536 spacing. Each sensor card will have a corresponding flow cell and each flow cell can be tied together by design or in a configurable manner using a manifold. The flow cells will be seated in a block as shown in FIG. 17 which will maintain the flow cell fluid at a precise design temperature.

Figure 18:
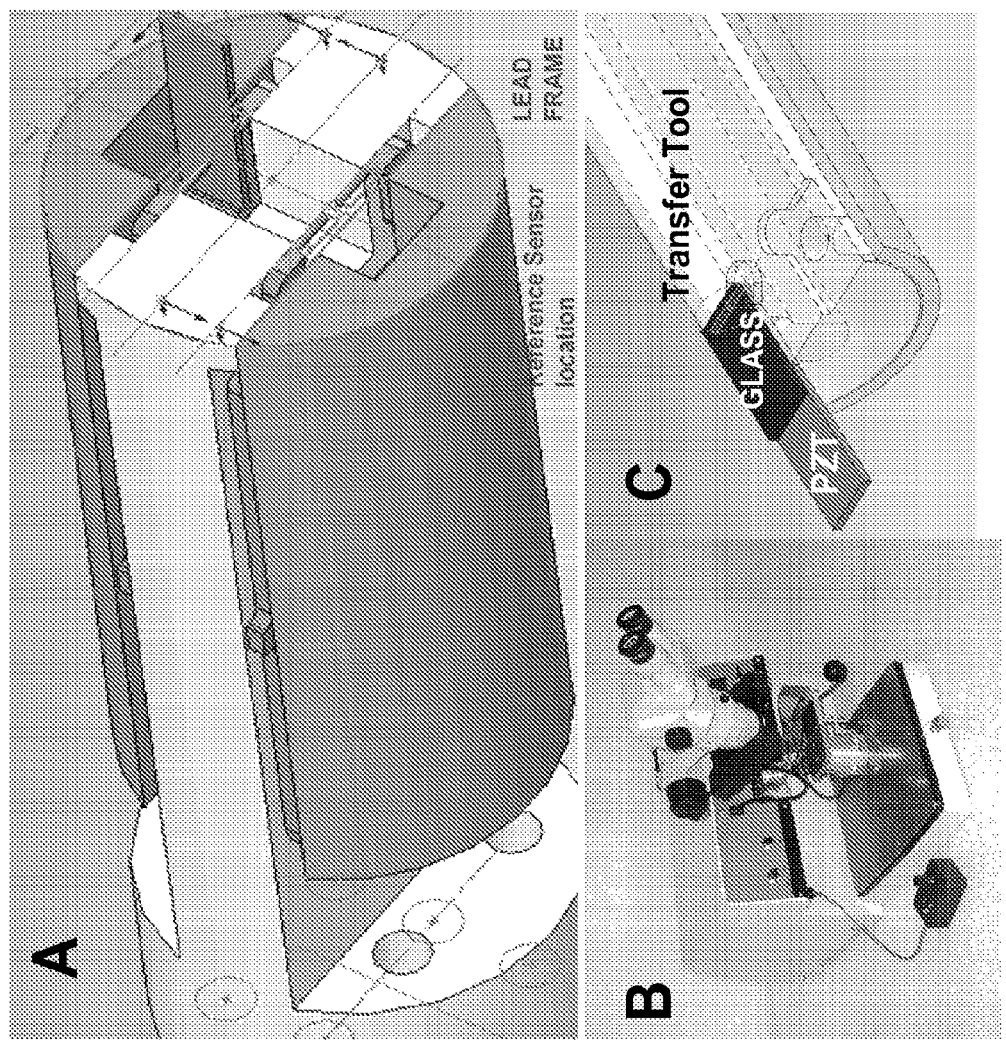
FIG. 18 is a depiction of an example sensor fabrication tool.

FIG. 18 is a depiction of an example sensor fabrication tool. The fabrication platform shown in FIG. 18 is a flexible fabrication platform that allows a full range of sensor geometries to be fabricated and evaluated. The sensor fabrication tool depicted in FIG. 18 is an example of universal design for investigating optimal sensor design parameters. In an example embodiment, the design involves use of photo-etched lead frames, precision solder or epoxy application, and precision machined parts. The assembly platform allows a variety of critical geometries to be fabricated. When coupled with the flexible sensor assembly design shown in FIG. 18, the fabrication platform will enable the optimal sensor design parameters to be identified which can subsequently be used to build reproducible sensors in an 8-array module having the optimum sensitivity and selectivity. Repeatability will be quantified by comparing resonance spectrum. In an example embodiment, a Westbond 7200CR manual die bonder (FIG. 18, inset B) is used to facilitate the handling and precise positioning of the PZT die, glass die, and solder paste dots. This equipment allows positioning resolution better than 1 micron. The PZT-glass-solder parts will be positioned and assembled on a transfer tool (FIG. 18, inset C) that can be used for the second Phase of the assembly which is the bonding of the PZT-glass-solder parts to the electrodes and sensor housing (FIG. 18, inset A). In an example embodiment, the electrodes are made from photo-etched copper or similar metal. The sensor head assembly containing two sensors (one will serve as reference) will be completed on a third assembly station that uses precision translation stages and custom designed tooling with a resolution better than 1 micron. The sensor head will be completed with the addition of a stainless steel sheath. The assembly system as described will also allow sensors to be fabricated in a cantilever or beam (both ends fixed) configuration. The results derived from the fabrication optimization will provide the design inputs for the refined 8-array sensor module that will be scalable for the anticipated development of 96-well and 384-well configuration.

To create reproducible sensors that achieve the best sensitivity observed in earlier sensor designs and assembly techniques, two elements are used. The first is a predictive design tool or transfer function that can provide design inputs for the most optimal design. Such software tools have been developed that show strong correlation between the model and fabricated sensors in terms of both resonance frequency as well as mass change sensitivity. The second is an assembly platform and sensor design that combines flexibility, precision, and repeatability necessary to explore the design inputs from the dynamic sensor model. FIG. 18 shows one sensor (labeled PZT) without the glass bonded to the top side of it. The reference sensor is to be located in the second slot that is labeled as reference sensor. Using a solid modeling software program, a universal sensor design will explore and identify optimal sensor design parameters. Example schematics of the PEMC sensor design are described above (See FIGS. 1 through 16). Detailed simulation studies have shown that the geometric parameters, e.g., the width ($W_P$) and the lengths ($L_P$, $L_{OL}$ and $L_{NP}$) influence resonance frequency values and their intensities (Q-values). For example when $W_P$ is 2 mm one finds a high order resonance mode near 600 kHz which exhibits sensitivity of 170 fg/Hz, and when $W_P$ was reduced to 1 mm sensitivity increased to 0.7 fg/Hz. The improvement in sensitivity was due to the emergence of a high-order resonance mode near 1 MHz.

In an example configuration, sensors that fall within a 1 kHz of resonance frequency were coated with polyurethane (PU) so that the PZT layer was electrically insulated. Spin coating at various rpm (100 to 3000 rpm; corresponding to 0.1 to 30 g) was used, and the coated sensors were oven cured at 80° C. for 24 hours. Spectral properties were measured post PU-coating. Subsequently, 100 nm Au was deposited and calibration using 11-mercaptoundecanoic acid (MUD) was carried out. Reproducibility of sensor array calibration was determined from dispersion of mass calibration data. Specifically, the data were fitted to the function $(-\Delta f) = A \log(C_0) + B$ where A and B are constants, $(-\Delta f)$ is sensor response and $C_0$ is mass of MUD added in the range of 1 ag to 1 pg. The variance in A and B values which characterize sensor response variation for a given geometry can be quantified. Ultimately variance data, namely accuracy of fabrication were determined as ±x %.

The geometric parameter (length) of a cantilever strongly influences resonance frequency. After finalizing the reproducible fabrication process, geometric parameters ($L_P$, $L_{OL}$ and $L_{NP}$) and solder location will be varied systematically based on already carried out finite element simulation to seek optimum sensitivity. Specifically, the length parameters will be varied about their nominal values (which give ~100 ag/Hz sensitivity), and the location of solder will be varied between the epoxy and the quartz layer. It has been observed that maximum electric field in PZT occurs at a fraction of a millimeter away from the fixed end of the cantilever (epoxy-end). A manually fabricated sensor with solder connection external to epoxy end exhibited sharp resonance near 2 MHz. One of them exhibited ~200 ag/Hz sensitivity. Sub femtogram/Hz sensitivity with routine fabrication is anticipated.

In one test configuration each sensor array module has 8 sensors in a linear array as shown in FIG. 17. Each sensor is immobilized with antibody specific to the target biomarker, while one sensor serves as the control or reference sensor (e.g., immobilized with anti-bovine serum albumin, or the like). Immobilization of an antibody is carried out in microplate wells so that each sensor is separated from the other during the chemical and biochemical treatment steps described below.

The sensing glass or quartz surface is thoroughly cleaned sequentially with a methanol-hydrochloric acid solution (1:1 v/v), concentrated sulfuric acid, hot sodium hydroxide, piranha solution and finally boiling water. The surface is rinsed between each washing step with deionized water. The cleaning procedure produces reactive hydroxyl groups on the glass surface. After cleaning, the glass surface is silanylated with 0.4% 3-aminopropyl-triethoxysilane (APTES; Sigma-Aldrich) in deionized water at pH 3.0 (adjusted with HCl) and 75° C. for 2 hours. APTES reacts with glass leaving free amines. Carboxylic groups present in the antibody are activated using the zero length cross linker 1-ethyl-3-(3-dimethylaminopropyl)-carbodiimide (EDC; Sigma-Aldrich) and promoted by sulfo-N-hydroxysuccinimide (Sigma-Aldrich). EDC converts carboxylic groups into reactive unstable intermediates susceptible to hydrolysis. Sulfo-NHS replaces EDC producing a more stable reactive intermediate that readily reacts with amines. Covalent coupling of the stable intermediate with the silanylated glass surface will be carried out at room temperature for 2 hours. Final concentration of activated antibody will be 10 μg/mL. The immobilization of antibodies on one of the sensors will be monitored. Data will be recorded and the decrease will enable estimation of surface density of immobilized antibody. At the end of immobilization the resonance frequency of each sensor in the array will be sequentially determined and recorded. The glass surface with the immobilized antibody will be used in detection experiments.

In an example configuration, the glass sensor surface is gold sputtered to 100 nm. It is rinsed with piranha solution for 90 seconds, followed by DI water rinse prior to washing in pure ethanol. For attaching to gold surface, first Protein G is immobilized by immersing the sensor array in 1 to 10 μg/mL Protein G solution for one hour. After a PBS rinse, the sensor is immersed in antibody bearing solution for an hour for immobilization to occur.

Figure 19:
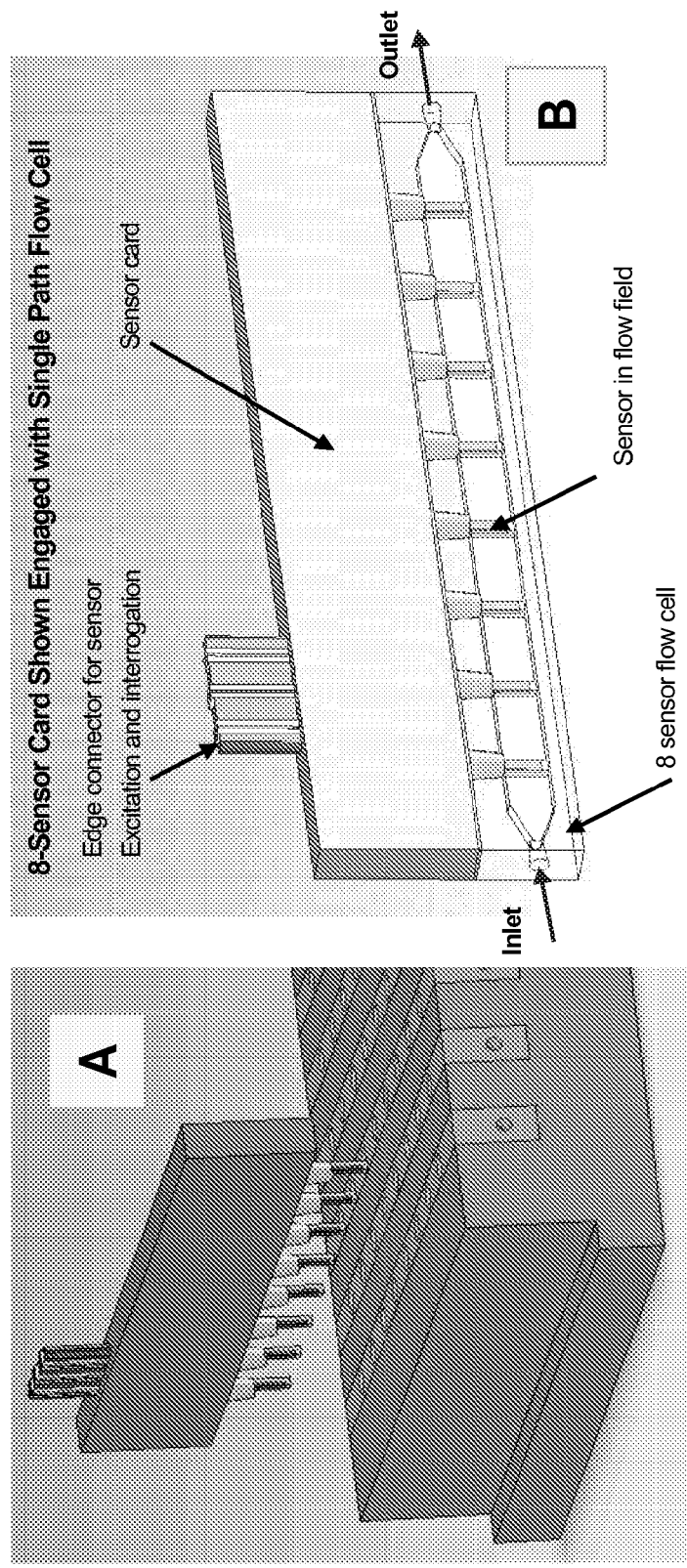
FIG. 19 is a depiction of an example flow cell.

In an example configuration, the 8-sensor array is installed in the flow cell shown in panel A of FIG. 19 and buffer flow is initiated. Panel A of FIG. 19 depicts a 96-well containing antibodies and an 8-sensor array module. Panel B shows the 8-sensor module mating with the flow cell via a conical fitting (e.g., luer) and the clearance is engineered to provide low hold up volume. Seven of the sensors are connected to the electronic module and one to an impedance analyzer.

Quantification Of A Target Analyte

Quantification of an amount of a target analyte accumulated on a sensor incorporates calibration of the sensor as part of the quantification process. Quantification is performed using a single sample to which amounts of the target analyte are added. Calibration is performed as part of quantification on the same sample. The target analyte is detectable and quantifiable using label free reagents and requiring no sample preparation. Thus, separate samples for calibration and quantification are not needed. There is no need for a "clean" or purified sample. For example, if a biomarker is being quantified in urine, a single sample of the patient's urine can be used for quantification. A clean (e.g., obtained from a laboratory and not the patient's urine) is not needed to calibrate the sensor.

The ability to measure low concentration of an analyte rapidly, inexpensively, and directly in a medium (e.g., a biomarker in blood serum) without the use of labeled reagents provides a novel and powerful diagnostic capability. This is particularly advantageous when applied to cancer biomarkers because many cancer biomarkers, at early stage of tumor development, are present at sub-picogram per mL concentration.

Figure 20:
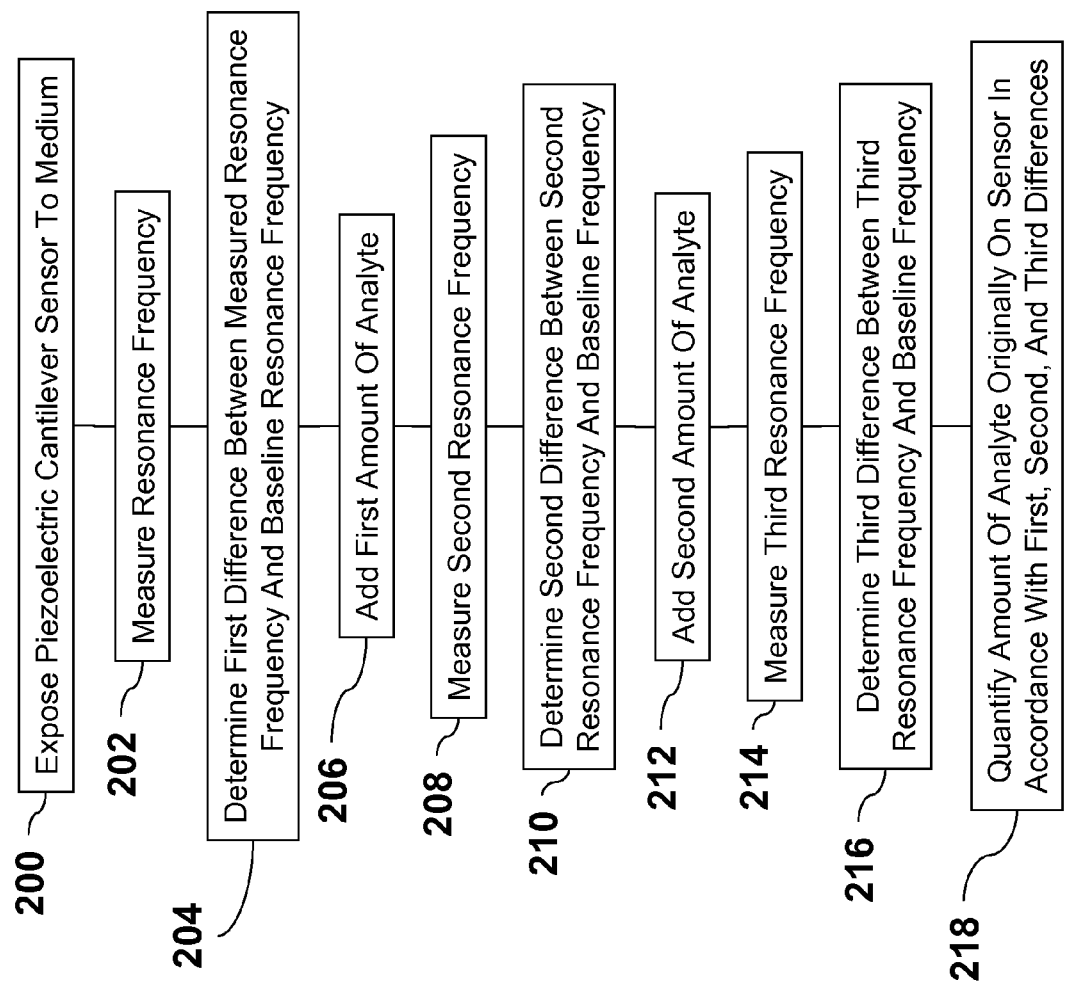
FIG. 20 is a flow diagram of an example quantification process.

FIG. 20 is a flow diagram depicting an example quantification process. At step 200, a portion of the piezoelectric cantilever sensor is exposed to a medium. The portion of the piezoelectric cantilever sensor is configured such that a target analyte will bind to the portion. When the portion of the piezoelectric sensor is exposed to the medium, at step 200, the target analyte may or may not be present in the medium, and the process depicted in FIG. 20 will quantify the amount, if any, in the medium. Binding can be accomplished in accordance with any of the techniques described herein. An analyte can include any appropriate analyte in the medium. For example, the biomarker can include any appropriate biomarker capable of providing an indication of a biological condition. In an example embodiment, a biomarker refers to cells and compounds that may be measured in a sample and used to indicate the presence of particular organism in the sample and/or to reflect a physiological or pathological state of the sample source. Suitable cells include, for example, tumor cells or microorganisms, such as bacteria. Accordingly, a microorganism may serve as a biomarker for the presence of a contaminant in a sample, such as food. Suitable compounds include, for example, nucleic acids, such as DNA and RNA, amino acids, peptides, proteins, lipids, carbohydrates, glycoproteins, glycolipid, or combinations thereof. Accordingly, a protein may serve as a biomarker for the presence of a pathological state, such as cancer, when measured in a sample from a subject. The medium can comprise any appropriate medium, such as for example, any fluid (liquid and/or gas), a body fluid, blood serum, a solid food sample, a liquid food sample, or the like.

At step 202, the resonance frequency of the piezoelectric cantilever sensor is determined. The difference between the measured resonance frequency and a baseline frequency is determined at step 204. The baseline frequency is the resonance frequency of the piezoelectric cantilever sensor having no target analyte bound thereto. At step 206, a first amount of the target analyte is added to the medium. At step 208, a second resonance frequency of the piezoelectric cantilever sensor is measured. And, at step 210, a second difference between the second resonance frequency and the baseline frequency is determined. A second amount of the target analyte is added to the medium at step 212 and a third resonance frequency of the piezoelectric cantilever sensor is measured at step 214. At step 216, a third difference between the third resonance frequency and the baseline frequency is determined. And, at step 218, the amount of the target analyte accumulated on the piezoelectric cantilever sensor during step 202 is determined in accordance with the first, second, and third differences.

The herein described quantification process utilizing a piezoelectric cantilever sensor has been applied to quantify various types of biomarkers. The piezoelectric cantilever utilized exhibited high-order modes at 900 kHz and 1.8 MHz. Both 900 kHz and 1.8 MHz peaks were used for detection experiments. The Q at 900 kHz in air was 67.9 and in phosphate buffered saline (PBS) 32.0 while at 1.8 MHz, Q in air was 14.6 and in PBS it was 12.0. These Q-values are sufficiently high such that the resonance frequency could be determined with an accuracy of $\pm 10$ to $\pm 25$ Hz, and were useful in detecting target analyte bound to the sensor surface. The sensitivity of measurement was observed to increase as the resonance frequency increased.

As an example application of the herein described quantification process, a description is provided below wherein the quantification process is utilized to quantify a cancer biomarker in urine. The quantification process required no sample preparation. Calibration and quantification were conducted on the same urine sample. No label reagents were needed.

A biomarker that has been identified as a specific and selective biomarker for prostate cancer is $\alpha$-Methylacyl-CoA racemase (AMACR), also known as P504S. AMACR has been reported to be one of the very few biomarkers that can distinguish cancer from benign cells with high sensitivity and specificity for prostatic carcinoma. AMACR is an enzyme that catalyzes the racemization of R-stereoisomers of branched-chain fatty acids to S-stereoisomers and plays an important role in peroxisomal $\beta$-oxidation of branched-chain fatty acids. AMACR is a cytoplasmic protein of 382 amino acids. The AMACR gene on chromosome 5 has been identified by several groups as a gene that is consistently up-regulated in prostate cancer at the mRNA and protein levels. AMACR is a sensitive marker for prostate cancer and is potentially a very valuable diagnostic tool for preventing biopsies and interpreting challenging biopsies. AMACR has been shown to be nearly absent in urine of patients without prostate cancer; thus making it a valuable biomarker for this disease. Because AMACR is present in voided urine of prostate cancer patients, a non-invasive molecular approach is utilized to detect AMACR stand alone and/or to augment the current screening methods.

AMACR was quantified utilizing a piezoelectric cantilever sensor, directly in patient urine without a sample preparation step and without the use of labeled reagents. Measurements were made under sample flow conditions (~0.1 cm/s) combined with active vibration of the sensing surface, which resulted in unparalleled selectivity in the complex fluid environment. Clean catch voided urine specimens were prospectively collected from five confirmed prostate cancer patients 3 weeks post biopsy. The presence of AMACR was measured in a blinded manner by exposing 3-mL of urine to the anti-AMACR immobilized piezoelectric cantilever sensor. The resonance frequency of piezoelectric cantilever sensor decreased as AMACR from sample binds to the antibody on the sensor. The resonance frequency changed for the five patients tested were 4,314±35 (n=2), 269±17 (n=2), 977±64 (n=3), 600±31 (n=2), and 801±81 (n=2) Hz, respectively. Positive detection was observed within ~15 minutes. The responses to positive, negative, and buffer controls were −9±13, −34±18 Hz and −6±18 Hz, respectively. Positive control is the response for a young adult urine in which AMACR was added at 1 pg/mL and the sensor was a bare one without the anti-AMACR antibody. Negative control is the sensor response to young adult urine exposed to sensor prepared with anti-AMACR. Positive verification of AMACR attachment was confirmed by low-pH buffer release. The sensor response was quantitatively related to AMACR concentration in control urine, and the relationship was used in developing an in situ calibration method for quantifying AMACR in patient urine. Estimated concentrations of 42, 2, and 3 fg/mL AMACR were calculated for the three patient urine, while absence of AMACR was confirmed in control urine (n=13). Because of simplicity of measurement combined with high sensitivity and specificity, the method may be a useful adjunct in a point-of-care setting to identify men at increased risk for prostate cancer.

Two AMACR-calibrations, one in PBS and the second in AMACR-free urine, were carried out at 0.5 mL/min. The antibody-immobilized sensor was installed and PBS solution was re-circulated until the resonance frequency stabilized. Three-mL samples containing 30 fg to 300 ng AMACR in PBS, were sequentially introduced in concentration steps of 10×, allowing steady state to be reached between changes. The steady state resonance frequencies are correlated to AMACR concentration using a mathematical model.

Calibration in urine was devised to eliminate the density effect. This was accomplished using control urine as the running buffer. First, three mL of control urine were introduced into the flow circuit in a recirculation mode, and the sensor was allowed to reach steady state resonance frequency. Then, a 100 μL standard of 100 fg/mL AMACR (10 fg) was introduced and the resulting sensor response was recorded. Subsequently, additional 100 μL standard of increasing concentration in 10× steps were added until the last addition of 100 ng/mL was done. The measured steady state resonance frequencies were then mathematically correlated to AMACR concentration.

Since urine is of highly variable composition, the following scheme was used for quantifying AMACR. An anti-AMACR immobilized sensor was inserted into a sensor flow cell (SFC) and stabilized in PBS. A 3-mL patient urine was introduced into the flow circuit in recirculation mode until steady state sensor response was reached. Since flow cell is 3 mL, the 3 mL urine effectively diluted the AMACR concentration by 50%. Once stabilized 100 μL of two known concentration of AMACR standards were added sequentially and the resonance frequency change was measured. The values of the two standards were chosen so that the sensor response was not in the saturated response region (>2000 Hz).

It is useful to obtain calibration values in urine itself. In order to eliminate the density effect noted above, a urine calibration method was devised that used control urine as the running buffer. Sensor response was obtained by spiking with known amounts of AMACR. As a result, an initial response to density change was observed, followed by a series of sensing responses relating to increasing mass of AMACR in the circulating urine buffer.

For quantification, the use of buffer medium calibration constants tends to under estimate the amount of AMACR present. Since urine is highly variable in its content, it is useful to use the patient's urine as the running buffer. Devised was a method of in situ calibration for quantifying AMACR in patient urine. The basis of this approach is to determine sensor response to two standard additions of AMACR with patient urine as the running buffer. In this approach, small mass additions were used so as not to saturate the sensor. The frequency response associated with the two knowns was used to calculate values of A and B below. The frequency shift due to the patient sample subtracting out the response due to density was then used to calculate the AMACR present. That is, $$(-\Delta f)_u = A\log(C_{b0u}) + B \tag{1}$$

$$(-\Delta f)_1 = A\log\left(C_{B0u} + \frac{\Delta m_1}{V}\right) + B \tag{2}$$

$$(-\Delta f)_2 = A\log\left(C_{B0u} + \frac{\Delta m_1 + \Delta m_2}{V}\right) + B \tag{3}$$

where $(-\Delta f)_u$, $(-\Delta f)_1$, and $(-\Delta f)_2$ are the density-corrected resonance frequency changes due to the patient urine and cumulative frequency response to known additions ($\Delta m_1$, $\Delta m_2$), respectively, $C_{b0u}$ is the AMACR concentration in patient urine and V is the total volume in the flow circuit.

Figure 21:
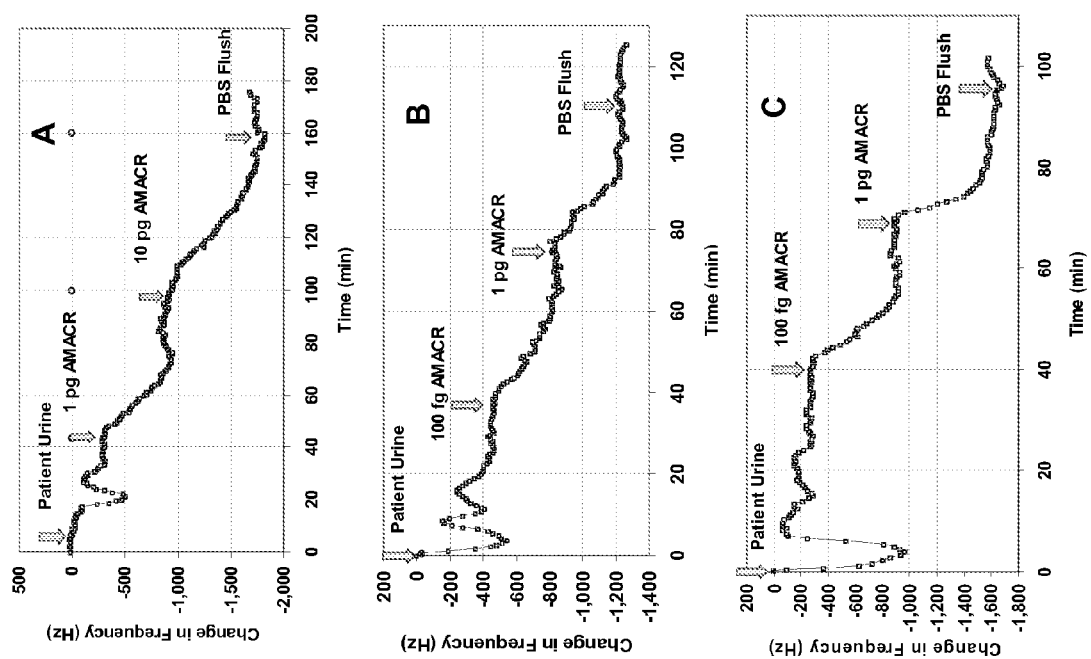
FIG. 21 depicts quantification of AMACR in patient urine in three patient samples.

Three patient samples were evaluated with the piezoelectric cantilever sensor using the above method and are shown in FIG. 21. In panel A is shown the frequency response of the piezoelectric cantilever sensor due to AMACR patient urine followed by 1 pg and 10 pg AMACR additions. The frequency decreases due to patient urine, 1 pg, and 10 pg AMACR were 315, 620, and 854 Hz, respectively. Using Eq. (2)-(4) AMACR concentration is estimated as 42 fg/mL in patient urine. In panel B is shown the frequency response of the piezoelectric cantilever sensor due to AMACR patient urine followed by 100 fg and 1 pg AMACR additions. The frequency decreases due to patient urine, 100 fg and 1 pg AMACR were 460, 392, and 362 Hz, respectively. An estimated AMACR concentration of 2 fg/mL was calculated for the patient urine. In panel C is shown the frequency responses of piezoelectric cantilever sensor due to AMACR patient urine followed by 100 fg and 1 pg AMACR additions are shown. The frequency decreases for the three cases are 274, 615, and 749 Hz, respectively. An estimated AMACR concentration of 3 fg/mL was calculated for the patient urine.

In all cases the density response at the end was small, but variable. In all cases, the urinary AMACR gave a fairly substantial decrease of 315, 460, and 274 Hz for the three patients. The frequency changes corresponded to 42, 2, and 3 fg/mL. Control urine gave a response of 10 Hz. The average concentration of AMACR in a patient suffering from prostatic adenocarcinoma is not available. The values determined in this study are below the detection limit of conventional immunoassays such as ELISA.

In an example embodiment, the ability to identify elevated levels of AMACR in patient urine may be seen as a complimentary assay to more traditional diagnostic tools such as DRE, PSA screening, and needle biopsy. The ability to rapidly (<60 minutes) identify the presence of low levels of AMACR in voided urine samples without any sample preparation provides a versatile analytical tool to determine patient risk of harboring prostate carcinoma. With the lack of specificity associated with PSA screening, and the inability to identify the initial stages of carcinoma with DRE, the piezoelectric cantilever sensor may be able to provide additional information by quantifying the presence of AMACR in urine samples in the outpatient (point of care) setting. This novel diagnostic ability has the potential to better stratify patients eligible for prostate biopsy. Since AMACR is known to be up-regulated in patients with prostate cancer, combining traditional diagnostic methods with real-time AMACR urine measurement may prove to be a useful screening tool.

Figure 22:
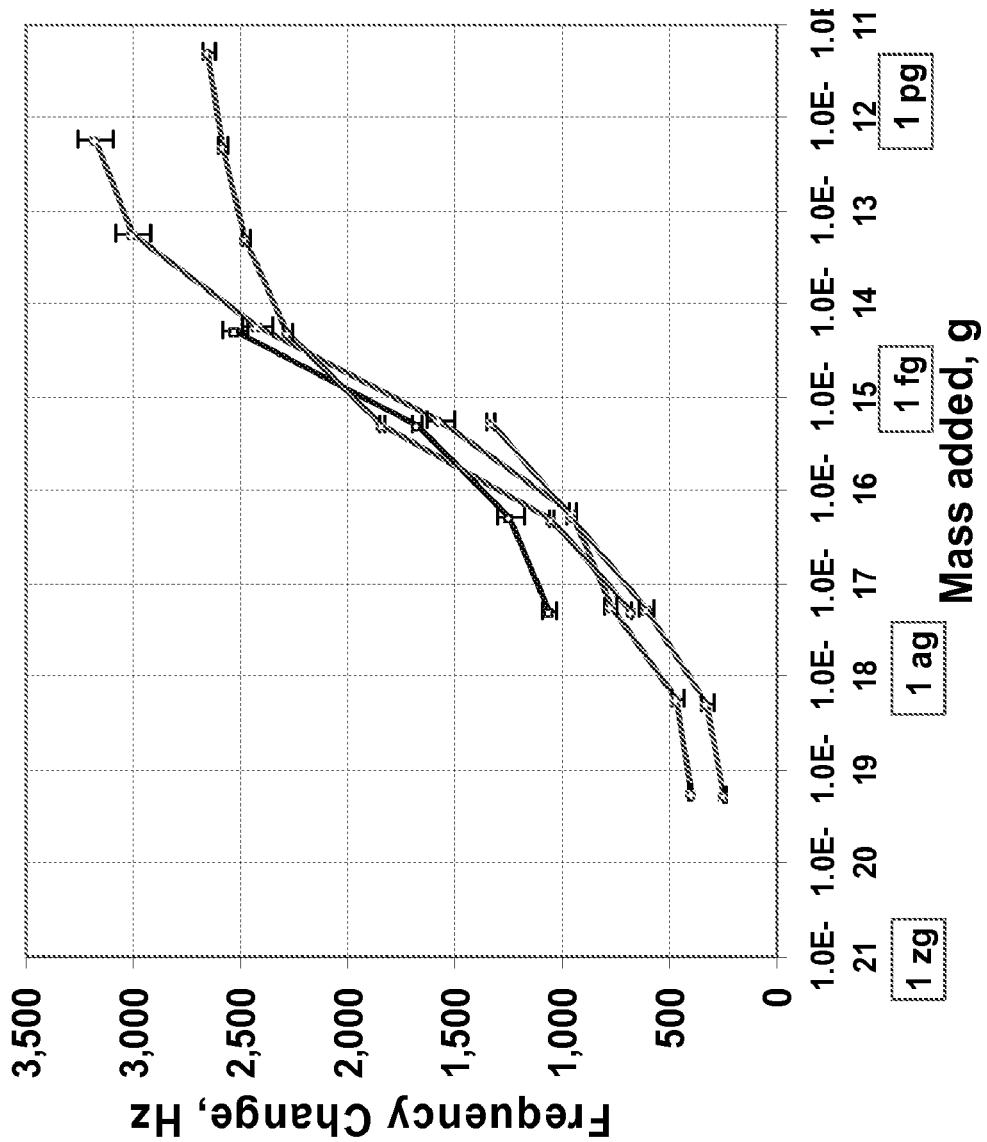
FIG. 22 depicts the results of calibrating the PEMC sensor mounted in a constant temperature incubator (dry) and 1 μL of aqueous dilute 11-mercaptoundecanoic acid (MUD) solution was dispensed on the Au-coated part of the sensor.

FIG. 22 depicts the results of calibrating the piezoelectric cantilever sensor mounted in a constant temperature incubator (dry) and 1 μL of aqueous dilute 11-mercaptoundecanoic acid (MUD) solution was dispensed on the Au-coated part of the sensor. Four sensors were tested. The resonance frequency decreased quite drastically and then recovered as the water evaporated, and reached a constant value. Sequential additions gave increasing attachment to the PEMC surface indicated by the decrease in recovered resonance frequency. Results indicate that it is possible to measure a 100 zeptogram change in a gas phase. The results of FIG. 22 indicate that the sensor response correlates with the mass of analyte bound to the sensor. The four sensor characteristics shown indicate that the nature of the response curve can be modified by altering sensor surface area of by the number of available binding sites on the sensor.

Other experiments were conducted to determine the sensitivity of the PEMC sensor. For example, experiments were conducted to detect *Escherichia coli* O157:H7 (EC) in the presence of spinach, spring lettuce mix, and ground beef wash and particulate matter. These experiments illustrated the effectiveness of the PEMC sensor with dirty samples. Experiments also were conducted to measure DNA hybridization at femtomolar concentration directly in human serum and in the presence of copious non-complementary DNA strands. Further experiments were conducted with the PEMC sensor to detect staphylococcal enterotoxin B in apple juice and milk.

Figure 23:
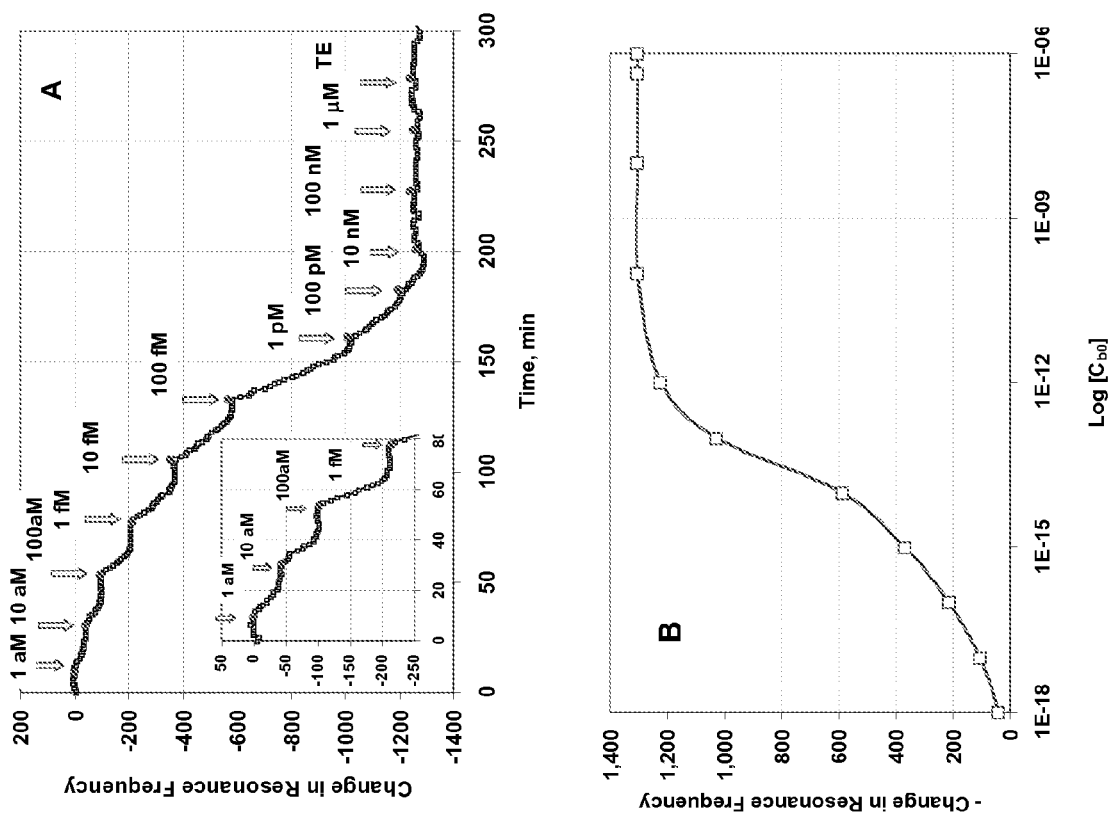
FIG. 23 is an example graph depicting results of measuring DNA hybridization concentration directly in human serum and in the presence of copious non-complementary strands.

FIG. 23 is an example graph depicting results of measuring DNA hybridization concentration directly in human serum and in the presence of copious non-complementary strands. The piezoelectric cantilever sensor response to probe immobilization is shown in FIG. 23. After initial stabilization, the reservoir containing 10 mL of 1 aM probe (HS—$C_6H_{12}$-5'-GGAAGAAGCTTGCTT-3') was introduced. The first 5 mL was flowed in a once through mode, and the last 5 mL was put in recirculation mode. The piezoelectric cantilever sensor responded, as shown in FIG. 23 with a decrease in resonance frequency as the probe's thiol group became bound to sensor surface forming a thiolated bond. After a transient period of ~13 minutes the sensor reached steady state with a total resonance frequency decrease of 42 Hz. The inset in plot A of FIG. 23 shows that the noise level is ~2 Hz. At 30 min, the sample was changed to 10 aM. Again, the first 5 mL was flowed in a once through mode followed by recirculating the last 5 mL. Since the flow circuit hold-up volume is 2.2 mL, 5 mL provided sufficient volume for removing the residuals. Resonance frequency decreased by an additional 47 Hz. The process was repeated in steps of 10× in concentration until there was no measurable resonance frequency response. The response (FIG. 23, plot A) suggests that the sensor surface became saturated at 100 pM. Increase of inlet concentration to 10 nM and then to 1 μM lead to no resonance frequency response indicating that no further probe immobilization took place. The changes in resonance frequency are plotted as a function of inlet probe concentration and the resulting curve (FIG. 23, plot B) indicates that a quantitative relationship exists between the surface and the liquid concentrations. The 10 mL of 1 aM solution contains a total of 6,000 molecules and weighs 51 ag. If it is assumed that all of them attached to the sensor, the mass change sensitivity (=mass change/resonance frequency change) is ~1 ag/Hz. Since the sensor is 1.8 mm$^2$ it has $1.1 \times 10^{13}$ Au<111> sites, and can accommodate a maximum of ~$3.2 \times 10^{11}$ ssDNA. Hence, chemisorption of 6,000 strands causes a fractional surface coverage on the order of $10^{-8}$. Note that ssDNA occupies a cross sectional area of 3.14 nm$^2$, and the values calculated are based on maximum packing density. A ten-fold increase in concentration (1 to 10 aM) causes a two-fold response (47 Hz to 47+57 Hz) suggesting a logarithmic response to the imposed concentration change. This is consistent with previous work with proteins and pathogens and the more recent work on chemisorption of thiols on the sensor surface. The higher level of sensitivity obtained (~1 ag/Hz) compared to the measured value (~300 ag/Hz) is in part due to nonlinear sensor response (FIG. 23, plot B). The wax calibration was done with the addition of 1 to 5 fg to the sensor surface. Closer examination of the results in FIG. 23, plot B shows that 1 fM gave a sensor response of ~370 Hz for an exposure to 51 fg of the probe. If we assume all the entering probe molecules attached to the surface, one would calculate the sensitivity as ~138 ag/Hz, which is in close agreement with the measured value of 300 ag/Hz.

As shown in FIG. 23, beyond 100 µM, the sensor response is saturated. It is noted that ten mL of 100 µM has $\sim 6 \times 10^{11}$ strands which is of approximate value of surface capacity of the sensor for ssDNA. That is, the observed saturation response (FIG. 23, plot B) is due to the fixed number of available sites for attachment. In work with smaller thiolic compounds a similar response was observed. From the results in FIG. 23 it is concluded that both mass addition method and probe chemisorption approach indicate that PEMC sensors exhibit sensitivity of sub-femtogram/Hz. The data in FIG. 23 indicate that the sensor response is quantitatively correlated with the sample analyte concentration. As in FIG. 22, the response curve can be modified by altering the area of the surface binding site density.

While illustrative embodiments of the quantification process wherein calibration is a part of the quantification process have been described, it is to be understood that other similar embodiments can be used or modifications and additions can be made to the described embodiment for performing quantification without deviating therefrom. Therefore, the quantification process should not be limited to any single embodiment, but rather should be construed in breadth and scope in accordance with the appended claims.

What is claimed:

1. A quantification method comprising:
    exposing a sensor to a quantity of a medium, wherein the sensor is configured to sense a target analyte;
    determining a first sensor response of the sensor subsequent to exposing the sensor to the quantity of the medium;
    adding a first amount of the target analyte to the quantity of the medium;
    determining a second sensor response of the sensor subsequent to adding the first amount;
    adding a second amount of the target analyte to the quantity of the medium;
    determining a third sensor response of the sensor subsequent to adding the second amount; and
    quantifying, in accordance with the first sensor response, the second sensor response, and the third sensor response, an amount of the target analyte sensed by the sensor prior to adding the first amount.

2. The method in accordance with claim 1, wherein the target analyte is unlabeled.

3. The method in accordance with claim 1, wherein the quantity of the medium requires no specific preparation.

4. The method in accordance with claim 1, wherein the sensor comprises a piezoelectric cantilever sensor.

5. The method in accordance with claim 4, further wherein:
    the first sensor response is determined in accordance with:
        measuring a resonance frequency of the piezoelectric cantilever sensor; and
        determining a first difference between the measured resonance frequency and a baseline frequency;
    the second sensor response is determined in accordance with:
        measuring a second resonance frequency of the piezoelectric cantilever sensor; and
        determining a second difference between the second measured resonance frequency and the baseline frequency; and
    the third sensor response is determined in accordance with:
        measuring a third resonance frequency of the piezoelectric cantilever sensor; and
        determining a third difference between the third measured resonance frequency and the baseline frequency.

6. The method in accordance with claim 1, wherein the medium comprises a body fluid, the method further comprising determining a condition of a donor of the body fluid in accordance with a result of the step of quantifying.

* * * * *